US008901276B2

(12) United States Patent
Wang et al.

(10) Patent No.: US 8,901,276 B2
(45) Date of Patent: Dec. 2, 2014

(54) PEPTIDE REAGENTS AND METHODS FOR DETECTION OF COLON DYSPLASIA

(75) Inventors: Thomas D. Wang, Ann Arbor, MI (US); Sharon Miller, Ann Arbor, MI (US); Bishnu Joshi, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 13/329,741

(22) Filed: Dec. 19, 2011

(65) Prior Publication Data

US 2012/0219505 A1    Aug. 30, 2012

Related U.S. Application Data

(60) Provisional application No. 61/425,062, filed on Dec. 20, 2010.

(51) Int. Cl.

| | | |
|---|---|---|
| *A61K 38/00* | (2006.01) | |
| *C07K 4/00* | (2006.01) | |
| *C07K 5/00* | (2006.01) | |
| *C07K 7/06* | (2006.01) | |
| *A61K 49/00* | (2006.01) | |
| *G01N 33/574* | (2006.01) | |
| *C07K 7/08* | (2006.01) | |
| *A61K 38/08* | (2006.01) | |
| *A61K 47/48* | (2006.01) | |
| *A61K 38/10* | (2006.01) | |

(52) U.S. Cl.
CPC .............. *C07K 7/06* (2013.01); *A61K 49/0002* (2013.01); *A61K 49/0041* (2013.01); *G01N 2800/52* (2013.01); *G01N 33/57419* (2013.01); *A61K 49/0043* (2013.01); *C07K 7/08* (2013.01); *A61K 49/0039* (2013.01); *A61K 38/08* (2013.01); *A61K 49/0032* (2013.01); *A61K 47/48246* (2013.01); *A61K 49/0056* (2013.01); *A61K 38/10* (2013.01)
USPC .............. 530/300; 424/9.1; 424/9.2; 424/9.3; 424/9.34; 424/9.4; 424/9.5; 514/19.3; 514/19.5; 514/19.8

(58) Field of Classification Search
None
See application file for complete search history.

(56) References Cited

U.S. PATENT DOCUMENTS

| | | | |
|---|---|---|---|
| 6,551,795 B1 * | 4/2003 | Rubenfield et al. | 435/69.1 |
| 6,605,709 B1 * | 8/2003 | Breton | 536/23.1 |
| 2003/0040466 A1 * | 2/2003 | Vodyanoy et al. | 514/7 |
| 2004/0031072 A1 * | 2/2004 | La Rosa et al. | 800/278 |
| 2004/0132108 A1 * | 7/2004 | Hupp et al. | 435/7.2 |
| 2006/0058228 A1 | 3/2006 | Kelly et al. | |
| 2009/0087878 A9 * | 4/2009 | La Rosa et al. | 435/69.1 |
| 2009/0136420 A1 | 5/2009 | Muller-Hermelink et al. | |
| 2009/0205085 A1 * | 8/2009 | Goldman et al. | 800/298 |
| 2011/0125029 A1 | 5/2011 | Wang et al. | |

OTHER PUBLICATIONS

Hsiung et al., "Detection of colonic dysplasia in vivo using a targeted heptapeptide and confocal microendoscopy," Nature Medicine 14:454-458 (2008).*
Hsiung et al., "Detection of colonic dysplasia in vivo using a targeted heptapeptide and confocal microendoscopy," Nature Medicine 14:454-458 (2008)—Supplementary figures and methods.*
Hsiung et al., "Detection of colonic dysplasia in vivo using a targeted heptapeptide and confocal microendoscopy," Nature Medicine 14:454-458 (2008)—copy provided with OA mailed May 17, 2013.*
Akyol et al., "Generating somatic mosaicism with a Cre recombinase—microsatellite sequence transgene", Nature Methods 5, 231-3 (2008).
Alencar et al., "Colonic Adenocarcinomas: Near-Infrared Microcatheter Imaging of Smart Probes for Early Detection—Study in Mice", Radiology, 244: 232-238 (2007).
Cwirla et al., "Peptides on phage: A vast library of peptides for identifying ligands", Proc. Natl. Acad. Sci. USA, 87:6378-6382 (1990).
Elahi et al., "Targeted imaging of colorectal dysplasia in living mice with fluorescence microendoscopy", Biomedical Optics Express, vol. 2, No. 4, pp. 981-986, Mar. 28, 2011.
Essler and Ruoslahti, "Molecular specialization of breast vasculature: A breast-homing phage-displayed peptide binds to aminopeptidase P in breast vasculature", Proc. Natl. Acad. Sci. USA, 99: 2252-2257 (2002).
Fields & Noble, "Solid phase peptide synthesis utilizing 9-fluorenylmethoxycarbonyl amno acids", Int. J. Pept. Protein Res, 35:161-214 (1990).
Hinoi et al., "Mouse Model of Colonic Adenoma-Carcinoma Progression Based on Somatic *Apc* Inactivation", Cancer Res., 67(20): 9721-9730 (2007).
Hsiung et al., "Detection of colonic dysplasia in vivo using a targeted heptapeptide and confocal microendoscopy", Nat. Med., 14: 454-458 (2008).
Hung et al., "Development of a mouse model for sporadic and metastatic colon tumors and its use in assessing drug treatment", Proc. Natl. Acad. Sci. USA, 107: 1565-1570 (2010).
Jemal et al., "Cancer Statistics, 2009", CA Cancer J Clin, 59:225-49 (2009).
Joyce et al., "Stage-specific vascular markers revealed by phage display in a mouse model of pancreatic islet tumorigenesis", Cancer Cell, 4: 393-403 (2003).

(Continued)

*Primary Examiner* — Christina Bradley
*Assistant Examiner* — Kristina M Hellman
(74) *Attorney, Agent, or Firm* — Marshall, Gerstein & Borun LLP

(57) ABSTRACT

The present invention is directed to peptide reagents, methods for detecting colon pre-cancer (dysplasia with non-polypoid or polypoid morphology) or cancer using the peptide reagents, and methods for targeting pre-cancerous or cancerous colon cells using the peptide reagents.

24 Claims, 4 Drawing Sheets

(56) References Cited

OTHER PUBLICATIONS

Kelly et al., "Detection of Invasive Colon Cancer Using a Novel, Targeted, Library-Derived Fluorescent Peptide", Cancer Res., 64:6247-51 (2004).

Lee et al., "Targeting Bladder Tumor Cells In Vivo and in the Urine with a Peptide Identified by Phage Display" Mol. Cancer Res., 5(1): 11-19 (2007).

Li et al., "Affinity Peptide for Targeted Detection of Dysplasia in Barrett's Esophagus", Gastroenterology, 139:1472-80 (2010).

Ludtke et al., "In vivo Selection and Validation of Liver-Specific Ligands Using a New T7 Phage Peptide Display System", Drug Deliv., 14: 357-369 (2007).

Mandava et al., "RELIC—A bioinformatics server for combinatorial peptide analysis and identification of protein-ligand interaction sites", Proteomics, 4: 1439-1460 (2004).

Mani, et al., "The Ubiquitin-Proteasome Pathway and Its Role in Cancer", Cancer; J Clin Oncol, 23,:4776-4789 (2005).

Miller et al., "In vivo fluorescence-based endoscopic detection of colon dysplasia in the mouse using a novel peptide probe", PLoS ONE, vol. 6, Issue 3, e17384, Mar. 8, 2011.

Pasqualini et al., "Organ targeting in vivo using phage display peptide libraries", Nature, 380:364-366 (1996).

Scott et al., "Searching for peptide ligands with an epitope library", Science, 249:386-390 (1990).

Su et al., "Multiple Intestinal Neoplasia Caused by a Mutation in the Murine Homolog of the APC Gene", Science 256(5057):668-670 (1992).

van Rijn et al.,"Polyp Miss Rate Determined by Tandem Colonoscopy: A Systematic Review", Am J Gastroenterol. 101:343-50 (2006).

Voutsadakis, "The ubiquitin-proteasome system in colorectal cancer", Biochim Biophys Acta, 1782:800-808 (2008).

Wang et al., "In vivo identification of colonic dysplasia using fluorescence endoscopic imaging", Gastrointestinal Endoscopy 1999; 49:447-55.

Zhao et al., "Identification of a Met-Binding Peptide from a Phage Display Library", Clin Cancer Res 13: 6049-6055 (2007).

International Search Report dated Aug. 29, 2012 for PCT/US2011/065804 filed Dec. 19, 2011.

\* cited by examiner

PEPTIDE REAGENTS AND METHODS FOR DETECTION OF COLON DYSPLASIA

This application claims the benefit of U.S. Provisional Patent Application No. 61/425,062 filed Dec. 20, 2010. The provisional application is hereby incorporated by reference in its entirety.

STATEMENT OF GOVERNMENT INTEREST

This invention was made with government support under U54 CA136429 and R01 CA142750 awarded by the National Institutes of Health. The government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 12 kilobytes ACII (Text) file named "45776A_SeqListing.txt," created on Dec. 14, 2011.

FIELD OF THE INVENTION

The present invention is directed to peptide reagents, methods for detecting colon pre-cancer (dysplasia with non-polypoid or polypoid morphology) or cancer using the peptide reagents, and methods for targeting pre-cancerous or cancerous colon cells using the peptide reagents.

BACKGROUND

Colorectal cancer (CRC) is one of the most common causes of cancer-related deaths in the world. In 2009, there were more than 146,000 new cases of colorectal cancer diagnosed, and colorectal cancer was the cause of nearly one out of every five cancer-related deaths in the United States. Jemal et al., *CA Cancer J Clin*, 59:225-49 (2009). White light colonoscopy is currently the primary method for performing colorectal cancer screening. This technique is sensitive to morphological changes in the mucosa, such as polyps and masses. However, this method is not sensitive to the detection of flat and depressed lesions, and the polyp miss rates can be as high as 22%. van Rijn et al., *Am J Gastroenterol.* 101:343-50 (2006). Adenomatous polyps, or adenomas, appear to be major precursors to CRC, even though only a fraction of adenomas progress to CRC. The transformation from pre-malignant mucosa to carcinoma occurs over a period of many years, thus providing window of opportunity for early detection. Furthermore, the presence of flat dysplastic lesions in the setting of chronic ulcerative colitis presents a significantly increased risk for the development of frank carcinoma.

Pre-clinical mouse models of disease provide an important tool for studying mechanisms of disease development. It has been established that mutations in the adenomatous polyposis coli (APC) gene are likely to be critical events in the initiation of the majority of adenomas and CRC. Previously-reported genetically engineered mouse models that mimic human APC gene mutations mainly develop adenomas in the small intestine (e.g., APC$^{Min}$ model, Su et al., *Science* 256(5057):668-670 (1992)), not the distal colon, making it difficult to image the polyps and their progression in vivo using currently available small animal endoscopy tools. Hinoi et al., *Cancer Res.*, 67(20): 9721-9730 (2007) describes genetically engineered mice (termed CPC:Apc mice) in which a somatic mutation in an Apc allele leads to a truncated Apc protein and causes the development of adenomas in the distal colon as early as 10 weeks. Others have developed mouse models that grow tumors in the distal colon using implantation of cancerous cells [Alencar et al., *Radiology*, 244: 232-238 (2007)] or adenovirus activated mutations [Hung et al., *Proc. Natl. Acad. Sci. USA*, 107: 1565-1570 (2010)] and report binding of cathepsin B smart probes, but surgical intervention was needed to generate polyps and the ensuing response to injury may have resulted in target alteration.

Endoscopic imaging with use of exogenous fluorescent-labeled probes, is a promising method for achieving greater specificity in the detection of neoplastic lesions by identifying the expression of unique molecular targets. Imaging provides precise localization, and fluorescence provides improved contrast. Previously, several diagnostic molecules have been used as targeted agents, including antibodies and antibody fragments, for the detection of pre-malignant and malignant lesions in various types of cancer. However, the use of antibodies and antibody fragments is limited by immunogenicity, cost of production and long plasma half-life. Small molecules, RNA aptamers, and activatable probes have also been used. Peptides represent a new class of imaging agent that is compatible with clinical use in the digestive tract, in particular with topical administration.

Phage display is a powerful combinatorial technique for peptide discovery that uses methods of recombinant DNA technology to generate a complex library of peptides, often expressing up to 107-109 unique sequences, that can bind to cell surface antigens. The DNA of candidate phages can be recovered and sequenced, elucidating positive binding peptides that can then be synthetically fabricated. Phage display identified peptide binders to high grade dysplasia in Barrett's esophagus [Li et al., Gastroenterology, 139:1472-80 (2010)] and human colonic dysplasia [Hsiung et al., Nat. Med., 14: 454-458 (2008)] using the commercially available NEB M13 phage system. The T7 system has proven effective in in vivo panning experiments identifying peptides specific to pancreatic islet vasculature [Joyce et al., Cancer Cell, 4: 393-403 (2003)], breast vasculature [Essler and Ruoslahti, Proc. Natl. Acad. Sci. USA, 99: 2252-2257 (2002)], bladder tumor cells [Lee et al., Mol. Cancer. Res., 5(1): 11-19 (2007)], and liver tissue [Ludtke et al., Drug Deliv., 14: 357-369 (2007)]. Panning with intact tissue presents additional relevant cell targets while accounting for subtle features in the tissue microenvironment that may affect binding.

Improved animal models for CRC and new products and methods for early detection of dysplasia are needed in the art. New products and methods for early detection would have important clinical applications for increasing the survival rate for CRC and reducing the healthcare costs.

DESCRIPTION

Transformed cells and tissues express molecular changes well in advance of gross morphological changes, thus providing a unique opportunity for the early detection of cancer. Peptides that bind to pre-cancerous colorectal lesions have the potential to guide tissue biopsy for lesions that are endoscopically "invisible," and such peptides can be isolated using combinatorial phage display screening. Peptides have in vivo advantages in the gastrointestinal tract because they can be delivered topically to identify early molecular changes on the surface of epithelial cells located on the most superficial layer of mucosa where cancer originates. In addition, they can exhibit rapid binding kinetics and also diffuse into diseased mucosa.

In one aspect, the invention provides peptides that bind to dysplastic colon cells and/or cancerous colon cells. Examples of peptides provided are NGTTSSNNQLINENNIQN (SEQ ID NO: 3), EHMYNTPHTYHTTMKNNK (SEQ ID NO: 4), QPIHPNNM (SEQ ID NO: 1), NKLAAALE (SEQ ID NO: 5), KNYKN (SEQ ID NO: 6), TNTHN (SEQ ID NO: 7) and KHTNN (SEQ ID NO: 8). Still other examples are SILPYPY (SEQ ID NO: 9), KCCFPAQ (SEQ ID NO: 2), YRAPWPP (SEQ ID NO: 10), QPWPTSI (SEQ ID NO: 11), WPTPPYA (SEQ ID NO: 12), MHAPPFY (SEQ ID NO: 13), VRPTLPM (SEQ ID NO: 22), NFMESLPRLGMH (SEQ ID NO: 23), HYKL (SEQ ID NO: 24), AKPGYLS (SEQ ID NO: 25), and LTTHYKL (SEQ ID NO: 26). Accordingly, a reagent is provided comprising a peptide consisting of an amino acid sequence selected from NGTTSSNNQLINENNIQN (SEQ ID NO: 3), EHMYNTPHTYHTTMKNNK (SEQ ID NO: 4), QPIHPNNM (SEQ ID NO: 1), NKLAAALE (SEQ ID NO: 5), KNYKN (SEQ ID NO: 6), TNTHN (SEQ ID NO: 7), KHTNN (SEQ ID NO: 8), SILPYPY (SEQ ID NO: 9), KCCFPAQ (SEQ ID NO: 2), YRAPWPP (SEQ ID NO: 10), QPWPTSI (SEQ ID NO: 11), WPTPPYA (SEQ ID NO: 12), MHAPPFY (SEQ ID NO: 13), VRPTLPM (SEQ ID NO: 22), NFMESLPRLGMH (SEQ ID NO: 23), HYKL (SEQ ID NO: 24), AKPGYLS (SEQ ID NO: 25), and LTTHYKL (SEQ ID NO: 26). The disclosure further provides a peptide consisting of an amino acid sequence selected from NGTTSSNNQLINENNIQN (SEQ ID NO: 3), EHMYNTPHTYHTTMKNNK (SEQ ID NO: 4), QPIHPNNM (SEQ ID NO: 1), NKLAAALE (SEQ ID NO: 5), KNYKN (SEQ ID NO: 6), TNTHN (SEQ ID NO: 7), KHTNN (SEQ ID NO: 8), SILPYPY (SEQ ID NO: 9), KCCFPAQ (SEQ ID NO: 2), YRAPWPP (SEQ ID NO: 10), QPWPTSI (SEQ ID NO: 11), WPTPPYA (SEQ ID NO: 12), MHAPPFY (SEQ ID NO: 13), VRPTLPM (SEQ ID NO: 22), NFMESLPRLGMH (SEQ ID NO: 23), HYKL (SEQ ID NO: 24), AKPGYLS (SEQ ID NO: 25), and LTTHYKL (SEQ ID NO: 26). Also provided is a reagent comprising a peptide consisting essentially of an amino acid sequence selected from NGTTSSNNQLINENNIQN (SEQ ID NO: 3), EHMYNTPHTYHTTMKNNK (SEQ ID NO: 4), QPIHPNNM (SEQ ID NO: 1), NKLAAALE (SEQ ID NO: 5), KNYKN (SEQ ID NO: 6), TNTHN (SEQ ID NO: 7), KHTNN (SEQ ID NO: 8), SILPYPY (SEQ ID NO: 9), KCCFPAQ (SEQ ID NO: 2), YRAPWPP (SEQ ID NO: 10), QPWPTSI (SEQ ID NO: 11), WPTPPYA (SEQ ID NO: 12), MHAPPFY (SEQ ID NO: 13), VRPTLPM (SEQ ID NO: 22), NFMESLPRLGMH (SEQ ID NO: 23), HYKL (SEQ ID NO: 24), AKPGYLS (SEQ ID NO: 25), and LTTHYKL (SEQ ID NO: 26). A peptide is also provided consisting essentially of an amino acid sequence selected from NGTTSSNNQLINENNIQN (SEQ ID NO: 3), EHMYNTPHTYHTTMKNNK (SEQ ID NO: 4), QPIHPNNM (SEQ ID NO: 1), NKLAAALE (SEQ ID NO: 5), KNYKN (SEQ ID NO: 6), TNTHN (SEQ ID NO: 7), KHTNN (SEQ ID NO: 8), SILPYPY (SEQ ID NO: 9), KCCFPAQ (SEQ ID NO: 2), YRAPWPP (SEQ ID NO: 10), QPWPTSI (SEQ ID NO: 11), WPTPPYA (SEQ ID NO: 12), MHAPPFY (SEQ ID NO: 13), VRPTLPM (SEQ ID NO: 22), NFMESLPRLGMH (SEQ ID NO: 23), HYKL (SEQ ID NO: 24), AKPGYLS (SEQ ID NO: 25), and LTTHYKL (SEQ ID NO: 26). Further a reagent is provided comprising a peptide comprising an amino acid sequence selected from NGTTSSNNQLINENNIQN (SEQ ID NO: 3), EHMYNTPHTYHTTMKNNK (SEQ ID NO: 4), QPIHPNNM (SEQ ID NO: 1), NKLAAALE (SEQ ID NO: 5), KNYKN (SEQ ID NO: 6), TNTHN (SEQ ID NO: 7), KHTNN (SEQ ID NO: 8), SILPYPY (SEQ ID NO: 9), KCCFPAQ (SEQ ID NO: 2), YRAPWPP (SEQ ID NO: 10), QPWPTSI (SEQ ID NO: 11), WPTPPYA (SEQ ID NO: 12), MHAPPFY (SEQ ID NO: 13), VRPTLPM (SEQ ID NO: 22), NFMESLPRLGMH (SEQ ID NO: 23), HYKL (SEQ ID NO: 24), AKPGYLS (SEQ ID NO: 25), and LTTHYKL (SEQ ID NO: 26). In still another aspect, a peptide is provided comprising an amino acid sequence selected from NGTTSSNNQLINENNIQN (SEQ ID NO: 3), EHMYNTPHTYHTTMKNNK (SEQ ID NO: 4), QPIHPNNM (SEQ ID NO: 1), NKLAAALE (SEQ ID NO: 5), KNYKN (SEQ ID NO: 6), TNTHN (SEQ ID NO: 7), KHTNN (SEQ ID NO: 8), SILPYPY (SEQ ID NO: 9), KCCFPAQ (SEQ ID NO: 2), YRAPWPP (SEQ ID NO: 10), QPWPTSI (SEQ ID NO: 11), WPTPPYA (SEQ ID NO: 12), MHAPPFY (SEQ ID NO: 13), VRPTLPM (SEQ ID NO: 22), NFMESLPRLGMH (SEQ ID NO: 23), HYKL (SEQ ID NO: 24), AKPGYLS (SEQ ID NO: 25), and LTTHYKL (SEQ ID NO: 26).

In a further aspect, the invention provides reagents comprising a peptide of the invention.

In some embodiments, the reagents comprise a detectable label attached to a peptide of the invention. The detectable label may be detectable, for example, by microscopy, ultrasound, PET, SPECT, or magnetic resonance imaging. In some embodiments the label detectable by microscopy is fluorescein isothiocyanate (FITC), 7-diethylaminocoumarin-3-carboxylic acid (DEAC), CF-633 or 5-carboxytetramethylrhodamine (TAMRA).

In some embodiments, a detectable label is attached to a peptide of the invention by a peptide linker. The terminal amino acid of the linker by be a lysine such as in the exemplary linker GGGSK (SEQ ID NO: 14). In certain aspects, the linker is an Ahx linker, an amino terminal linker comprising 6-amino hexanoic acid.

In other embodiments, the reagents comprise a therapeutic moiety attached to a peptide of the invention. The therapeutic moiety may be a chemopreventative or chemotherapeutic agent. In certain embodiments, the therapeutic moiety is celecoxib, 5-fluorouracil, and/or chlorambucil.

In yet a further aspect, the invention provides a composition comprising a reagent of the invention and a pharmaceutically acceptable excipient.

In still a further aspect, the invention provides a method for detecting colon dysplasia in a patient comprising the steps of administering a reagent comprising a peptide of the invention attached to a detectable label to the colon of the patient and detecting binding of the reagent to dysplastic cells. In some embodiments, the detectable binding takes place in vivo. In others, the detectable binding takes places in vitro. In still others, the detectable binding takes place in situ. In the colon, the transformation from pre-malignant mucosa to carcinoma involves the development of flat and depressed (non-polypoid) lesions, adenomatous polyps (polypoid lesions) and then frank carcinoma (colon cancer cells). Detecting colon dysplasia (i.e., dysplastic cells) according to the invention includes detecting binding to flat and depressed lesions, adenomatous polyps and/or cancer cells. In some embodiments, a reagent of the invention specifically detects cells of flat and depressed lesions. In some embodiments, a reagent of the invention specifically detects cells of adenomatous polyps. In some embodiments, a reagent of the invention specifically detects colon cancer cells. In some embodiments, a reagent of the invention may specifically detect two or more of cells of flat and depressed lesions, cells of adenomatous polyps and colon cancer cells. The phrase "specifically detects" means that the reagent binds to and is detected in association with a type of cell, and the reagent does not bind to and is not detected in association with another type of cell at the level of sensitivity at which the method is carried out.

Flat dysplastic lesions are also observed in the setting of chronic ulcerative colitis and are also contemplated to be detectable by methods of the invention.

In an additional aspect, the invention provides a method of determining the effectiveness of a treatment for colon cancer and/or cancer metastasis, or recurrence of cancer in a patient comprising the step of administering a reagent comprising a peptide of the invention attached to a detectable label to the colon of the patient, visualizing a first amount of cells labeled with the reagent, and comparing the first amount to a previously-visualized second amount of cells labeled with the reagent, wherein a decrease in the first amount cells labeled relative to the previously-visualized second amount of cells labeled is indicative of effective treatment. In some embodiments, a decrease of 5% is indicative of effective treatment. In other embodiments, a decrease of about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or more is indicative of effective treatment. In some embodiments, the method further comprises obtaining a biopsy of the cells labeled by the reagent.

In another aspect, the invention provides a method for delivering a therapeutic agent to dysplastic colon cells of a patient comprising the step of administering a reagent comprising a peptide of the invention attached to a therapeutic moiety to the patient.

In yet another aspect, the invention provides a method for delivering a therapeutic agent to colon cancer cells of a patient comprising the step of administering a reagent comprising a peptide of the invention attached to a therapeutic moiety to the patient.

In still another aspect, the invention provides a kit for administering a composition of the invention to a patient in need thereof, where the kit comprises a composition of invention, instructions for use of the composition and a device for administering the composition to the patient.

Linkers, Peptides and Peptide Analogs

As used herein, a "linker" is a sequence of amino acids, generally uncharged, located at a terminus of a polypeptide of the disclosure. In some embodiments, the linker sequence terminates with a lysine residue. Uncharged amino acids contemplated by the present disclosure include, but are not limited to, glycine, serine, cysteine, threonine, histidine, tyrosine, asparagine, and glutamine.

In some embodiments, the presence of a linker results in at least a 1% increase in detectable binding of a reagent of the invention to dysplastic colon cells or cancerous colon cells compared to the detectable binding of the reagent in the absence of the linker. In various aspects, the increase in detectable binding is at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, at least about 50-fold, at least about 100-fold or more.

The term "peptide" refers to molecules of 2 to 50 amino acids, molecules of 3 to 20 amino acids, and those of 6 to 15 amino acids. Peptides and linkers as contemplated by the invention may be 5 amino acids in length. In various aspects, a polypeptide or linker may be 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acids in length.

Exemplary peptides are, in various aspects, randomly generated by methods known in the art, carried in a polypeptide library (for example and without limitation, a phage display library), derived by digestion of proteins, or chemically synthesized. Peptides exemplified in the present disclosure have been developed using techniques of phage display, a powerful combinatorial method that uses recombinant DNA technology to generate a complex library of polypeptides for selection by preferential binding to cell surface targets [Scott et al., *Science*, 249:386-390 (1990)]. The protein coat of bacteriophage, such as the filamentous M13 or icosahedral T7, is genetically engineered to express a very large number ($>10^9$) of different polypeptides with unique sequences to achieve affinity binding [Cwirla et al., *Proc. Natl. Acad. Sci. USA*, 87:6378-6382 (1990)]. Selection is then performed by biopanning the phage library against cultured cells and tissues that over express the target. The DNA sequences of these candidate phage are then recovered and used to synthesize the polypeptide [Pasqualini et al., *Nature*, 380:364-366 (1996)]. The polypeptides that preferentially bind to dysplastic mucosa are optionally labeled with fluorescence dyes, including but not limited to, FITC, Cy 5.5, Cy 7, and Li-Cor. These polypeptide-dye reagents have been developed and have demonstrated preferential binding to colon cancer (HT29) cells in culture and to pre-clinical xenograft models [Kelly et al., *Cancer Res.*, 64:6247-51 (2004)].

Peptides include D and L forms, either purified or in a mixture of the two forms. Also contemplated by the present disclosure are peptides that compete with peptides of the invention for binding to colon cells.

In some embodiments, a peptide of a reagent of the invention is presented in multimer form. Various scaffolds are known in the art upon which multiple peptides can be presented. In one exemplary embodiment herein, peptide AKPGYLS (SEQ ID NO: 25) is presented in multimer form on a trilysine dendritic wedge. Other scaffolds known in the art include, but are not limited to, other dendrimers and polymeric (e.g., PEG) scaffolds.

It will be understood that peptides and linkers of the invention optionally incorporate modifications known in the art and that the location and number of such modifications are varied to achieve an optimal effect.

In some embodiments, the compound is a peptide analog having a structure based on one of the peptides disclosed herein (the "parent peptide") but differs from the parent peptide in one or more respects. Accordingly, as appreciated by one of ordinary skill in the art, the teachings regarding the parent peptides provided herein may also be applicable the peptide analogs.

In some embodiments, the peptide analog comprises the structure of a parent peptide, except that the peptide analog comprises one or more non-peptide bonds in place of peptide bond(s). In some embodiments, the peptide analog comprises in place of a peptide bond, an ester bond, an ether bond, a thioether bond, an amide bond, and the like. In some embodiments, the peptide analog is a depsipeptide comprising an ester linkage in place of a peptide bond.

In some embodiments, the peptide analog comprises the structure of a parent peptide described herein, except that the peptide analog comprises one or more amino acid substitutions, e.g., one or more conservative amino acid substitutions. Conservative amino acid substitutions are known in the art, and include amino acid substitutions in which one amino acid having certain physical and/or chemical properties is exchanged for another amino acid that has the same chemical or physical properties. For instance, the conservative amino acid substitution may be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

In some aspects, the peptide analog comprises one or more synthetic amino acids, e.g., an amino acid non-native to a mammal. Synthetic amino acids include β-alanine (β-Ala), N-α-methyl-alanine (Me-Ala), aminobutyric acid (Abu), γ-aminobutyric acid (γ-Abu), aminohexanoic acid (ε-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethyl-cysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met (O)), methionine-sulfone (Met($O_2$)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe (4-Cl)), 4-fluorophenylalanine (Phe(4-F)), 4-nitrophenylalanine (Phe(4-$NO_2$)), 4-cyanophenylalanine ((Phe(4-CN)), phenylglycine (Phg), piperidinylalanine, piperidinylglycine, 3,4-dehydroproline, pyrrolidinylalanine, sarcosine (Sar), selenocysteine (Sec), O-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2,3,4,-tetrahydro-isoquinoline-3-carboxylic acid (Tic), tetrahydropyranglycine, thienylalanine (Thi), O-benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (Me-Val), and alkylated 3-mercaptopropionic acid.

In some embodiments, the peptide analog comprises one or more non-conservative amino acid substitutions and the peptide analog still functions to a similar extent, the same extent, or an improved extent as the parent peptide. In certain embodiments, the peptide analog comprising one or more non-conservative amino acid substitutions exhibits about the same or greater binding to the colon cell in comparison to the parent peptide.

In some embodiments, the peptide analog comprises one or more amino acid insertions or deletions, in comparison to the parent peptide described herein. In some embodiments, the peptide analog comprises an insertion of one or more amino acids in comparison to the parent peptide. In some embodiments, the peptide analog comprises a deletion of one or more amino acids in comparison to the parent peptide. In some embodiments, the peptide analog comprises an insertion of one or more amino acids at the N- or C-terminus in comparison to the parent peptide. In some embodiments, the peptide analog comprises a deletion of one or more amino acids at the N- or C-terminus in comparison to the parent peptide. In these embodiments, the peptide analog still exhibits about the same or greater binding to colon cells in comparison to the parent peptide.

Detectable Markers

As used herein, a "detectable marker" is any label that can be used to identify the binding of a composition of the disclosure to colon tissue. Non-limiting examples of detectable markers are fluorophores, chemical or protein tags that enable the visualization of a polypeptide. Visualization in certain aspects is carried out with the naked eye, or a device (for example and without limitation, an endoscope) and may also involve an alternate light or energy source.

Fluorophores, chemical and protein tags that are contemplated for use in the invention include, but are not limited to, FITC, Cy 5.5, Cy 7, Li-Cor, a radiolabel, biotin, luciferase, 1,8-ANS (1-Anilinonaphthalene-8-sulfonic acid), 1-Anilinonaphthalene-8-sulfonic acid (1,8-ANS), 5-(and-6)-Carboxy-2',7'-dichlorofluorescein pH 9.0, 5-FAM pH 9.0, 5-ROX (5-Carboxy-X-rhodamine, triethylammonium salt), 5-ROX pH 7.0, 5-TAMRA, 5-TAMRA pH 7.0, 5-TAMRA-MeOH, 6 JOE, 6,8-Difluoro-7-hydroxy-4-methylcoumarin pH 9.0, 6-Carboxyrhodamine 6G pH 7.0, 6-Carboxyrhodamine 6G, hydrochloride, 6-HEX, SE pH 9.0, 6-TET, SE pH 9.0, 7-Amino-4-methylcoumarin pH 7.0, 7-Hydroxy-4-methylcoumarin, 7-Hydroxy-4-methylcoumarin pH 9.0, Alexa 350, Alexa 405, Alexa 430, Alexa 488, Alexa 532, Alexa 546, Alexa 555, Alexa 568, Alexa 594, Alexa 647, Alexa 660, Alexa 680, Alexa 700, Alexa Fluor 430 antibody conjugate pH 7.2, Alexa Fluor 488 antibody conjugate pH 8.0, Alexa Fluor 488 hydrazide-water, Alexa Fluor 532 antibody conjugate pH 7.2, Alexa Fluor 555 antibody conjugate pH 7.2, Alexa Fluor 568 antibody conjugate pH 7.2, Alexa Fluor 610 R-phycoerythrin streptavidin pH 7.2, Alexa Fluor 647 antibody conjugate pH 7.2, Alexa Fluor 647 R-phycoerythrin streptavidin pH 7.2, Alexa Fluor 660 antibody conjugate pH 7.2, Alexa Fluor 680 antibody conjugate pH 7.2, Alexa Fluor 700 antibody conjugate pH 7.2, Allophycocyanin pH 7.5, AMCA conjugate, Amino Coumarin, APC (allophycocyanin), Atto 647, BCECF pH 5.5, BCECF pH 9.0, BFP (Blue Fluorescent Protein), Calcein, Calcein pH 9.0, Calcium Crimson, Calcium Crimson Ca2+, Calcium Green, Calcium Green-1 Ca2+, Calcium Orange, Calcium Orange Ca2+, Carboxynaphthofluorescein pH 10.0, Cascade Blue, Cascade Blue BSA pH 7.0, Cascade Yellow, Cascade Yellow antibody conjugate pH 8.0, CFDA, CFP (Cyan Fluorescent Protein), CI-NERF pH 2.5, CI-NERF pH 6.0, Citrine, Coumarin, Cy 2, Cy 3, Cy 3.5, Cy 5, CyQUANT GR-DNA, Dansyl Cadaverine, Dansyl Cadaverine, MeOH, DAPI, DAPI-DNA, Dapoxyl (2-aminoethyl) sulfonamide, DDAO pH 9.0, Di-8 ANEPPS, Di-8-ANEPPS-lipid, DiI, DiO, DM-NERF pH 4.0, DM-NERF pH 7.0, DsRed, DTAF, dTomato, eCFP (Enhanced Cyan Fluorescent Protein), eGFP (Enhanced Green Fluorescent Protein), Eosin, Eosin antibody conjugate pH 8.0, Erythrosin-5-isothiocyanate pH 9.0, eYFP (Enhanced Yellow Fluorescent Protein), FDA, FITC antibody conjugate pH 8.0, FlAsH, Fluo-3, Fluo-3 $Ca^{2+}$, Fluo-4, Fluor-Ruby, Fluorescein, Fluorescein 0.1 M NaOH, Fluorescein antibody conjugate pH 8.0, Fluorescein dextran pH 8.0, Fluorescein pH 9.0, Fluoro-Emerald, FM 1-43, FM 1-43 lipid, FM 4-64, FM 4-64, 2% CHAPS, Fura Red $Ca^{2+}$, Fura Red, high Ca, Fura Red, low Ca, Fura-2 Ca2+, Fura-2, Fura-2, GFP (S65T), HcRed, Indo-1 $Ca^{2+}$, Indo-1, Ca free, Indo-1, Ca saturated, JC-1, JC-1 pH 8.2, Lissamine rhodamine, Lucifer Yellow, CH, Magnesium Green, Magnesium Green Mg2+, Magnesium Orange, Marina Blue, mBanana, mCherry, mHoneydew, mOrange, mPlum, mRFP, mStrawberry, mTangerine, NBD-X, NBD-X, MeOH, NeuroTrace 500/525, green fluorescent Nissl stain-RNA, Nile Blue, Nile Red, Nile Red-lipid, Nissl, Oregon Green 488, Oregon Green 488 antibody conjugate pH 8.0, Oregon Green 514, Oregon Green 514 antibody conjugate pH 8.0, Pacific Blue, Pacific Blue antibody conjugate pH 8.0, Phycoerythrin, R-Phycoerythrin pH 7.5, ReAsH, Resorufin, Resorufin pH 9.0, Rhod-2, Rhod-2 $Ca^{2+}$, Rhodamine, Rhodamine 110, Rhodamine 110 pH 7.0, Rhodamine 123, MeOH, Rhodamine Green, Rhodamine phalloidin pH 7.0, Rhodamine Red-X antibody conjugate pH 8.0, Rhodamine Green pH 7.0, Rhodol Green antibody conjugate pH 8.0, Sapphire, SBFI-Na+, Sodium Green Na+, Sulforhodamine 101, Tetramethylrhodamine antibody conjugate pH 8.0, Tetramethylrhodamine dextran pH 7.0, and Texas Red-X antibody conjugate pH 7.2.

Non-limiting examples of chemical tags contemplated by the invention include radiolabels. For example and without limitation, radiolabels that contemplated in the compositions and methods of the present disclosure include $^{11}C$, $^{13}N$, $^{15}O$, $^{18}F$, $^{32}P$, $^{52}Fe$, $^{62}Cu$, $^{64}Cu$, $^{67}Cu$, $^{67}Ga$, $^{68}Ga$, $^{86}Y$, $^{89}Zr$, $^{90}Y$, $^{94m}TC$, $^{94}Tc$, $^{95}Tc$, $^{99m}Tc$, $^{103}Pd$, $^{105}Rh$, $^{109}Pd$, $^{111}Ag$, $^{111}In$, $^{123}I$, $^{124}I$, $^{125}I$, $^{131}I$, $^{140}La$, $^{149}Pm$, $^{153}Sm$, $^{154-159}Gd$, $^{165}Dy$, $^{166}Dy$, $^{166}Ho$, $^{169}Yb$, $^{175}Yb$, $^{175}Lu$, $^{177}Lu$, $^{186}Re$, $^{188}Re$, $^{192}Ir$, $^{198}Au$, $^{199}Au$, and $^{212}Bi$.

A worker of ordinary skill in the art will appreciate that there are many such detectable markers that can be used to visualize a composition of the disclosure, in vitro, in vivo or ex vivo.

Therapeutic Moieties

Therapeutic moieties contemplated by the invention include, but are not limited to polypeptides or peptides, small molecules, therapeutic agents, chemotherapeutic agents, or combinations thereof.

The term "small molecule", as used herein, refers to a chemical compound, for instance a peptidometic or oligonucleotide that may optionally be derivatized, or any other low molecular weight organic compound, either natural or synthetic.

By "low molecular weight" is meant compounds having a molecular weight of less than 1000 Daltons, typically between 300 and 700 Daltons. Low molecular weight compounds, in various aspects, are about 100, about 150, about 200, about 250, about 300, about 350, about 400, about 450, about 500, about 550, about 600, about 650, about 700, about 750, about 800, about 850, about 900, about 1000 or more Daltons.

In some aspects, the therapeutic moiety is a protein therapeutic. Protein therapeutics include, without limitation, cellular or circulating proteins as well as fragments and derivatives thereof. Still other therapeutic moieties include polynucleotides, including without limitation, protein coding polynucleotides, polynucleotides encoding regulatory polynucleotides, and/or polynucleotides which are regulatory in themselves. Optionally, the compositions comprise a combination of the compounds described herein.

In various aspects, protein therapeutics include cytokines or hematopoietic factors including without limitation IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IL-7, IL-8, IL-9, IL-10, IL-12, IL-13, IL-14, IL-15, IL-16, IL-17, IL-18, thrombopoietin (TPO), angiopoietins, for example Ang-1, Ang-2, Ang-4, Ang-Y, the human angiopoietin-like polypeptide, vascular endothelial growth factor (VEGF), angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor, cytokine-induced neutrophil chemotactic factor 1, cytokine-induced neutrophil, chemotactic factor 2α, cytokine-induced neutrophil chemotactic factor 2β,β endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor α1, glial cell line-derived neutrophic factor receptor α2, growth related protein, growth related protein α, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor receptor, TNF, including TNF0, TNF1, TNF2, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, vascular endothelial growth factor, and chimeric proteins and biologically or immunologically active fragments thereof.

Therapeutic moieties also include, as one embodiment, chemotherapeutic agents. A chemotherapeutic agent contemplated for use in a reagent of the invention includes, without limitation, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinium coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

Dosages of the therapeutic moiety or reagent provided are administered as a dose measured in, for example, mg/kg. Contemplated mg/kg doses of the disclosed therapeutics include about 1 mg/kg to about 60 mg/kg. Specific ranges of doses in mg/kg include about 1 mg/kg to about 20 mg/kg, about 5 mg/kg to about 20 mg/kg, about 10 mg/kg to about 20 mg/kg, about 25 mg/kg to about 50 mg/kg, and about 30 mg/kg to about 60 mg/kg. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

"Effective amount" as used herein refers to an amount of a reagent of the invention sufficient to visualize the identified disease or condition, or to exhibit a detectable therapeutic or inhibitory effect. The effect is detected by, for example, an improvement in clinical condition or reduction in symptoms. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

Visualization of Reagents

Visualization of binding to colon cells is by any means known to those of ordinary skill in the art. As discussed herein, visualization is, for example and without limitation, in vivo, in vitro, or in situ visualization.

In one embodiment, visualization is performed via imaging and may be performed with a wide area endoscope (Olympus Corporation, Tokyo, Japan) that is designed specifically to collect fluorescence images with high spatial resolution over large mucosal surface areas on the macroscopic scale (millimeters to centimeters). This capability is needed to rapidly screen large surface areas such as that found in the distal esophagus during endoscopy to localize regions suspicious for disease [Wang et al., Gastrointestinal Endoscopy 1999; 49:447-55]. This technique has been adapted for fluorescence detection, and is compatible with dye-labeled probes. This instrument can image in three different modes, including white light (WL), narrowband imaging (NBI), and fluorescence imaging. Narrow-band imaging is a new technology that represents a variation of conventional white light illumination by altering the spectrum with optical filters to restrict or narrow the range of wavelengths.

The method enhances contrast in the endoscopic images to provide more visual details of the esophageal mucosa by tuning the light to maximize absorption of hemoglobin present in the vasculature of regions of intestinal metaplasia. The WL and NBI images are collected by the central objective lens, and the fluorescence image is collected by a second objective lens located near the periphery. There is a distance of approximately 3 mm between the centers of the white light and fluorescence objectives that results in only a slight misregistration of the two images. Furthermore, there is an air/water nozzle that removes debris from the objective lenses, and a 2.8 mm diameter instrument channel that can be used to deliver biopsy forceps. The objectives are forward viewing and have a field of view (FOV), defined by maximum angle of illumination, of 140 deg. The WL/NBI imaging modes have a depth of field (DOF), defined by range of distances between the distal end of the endoscope to the mucosal surface whereby the image is in focus, of 7 to 100 mm, and that for fluorescence is 5 to 100 mm. The transverse resolution measured at a distance of 10 mm from the mucosa for WL/NBI is 15 μm and for fluorescence is 20 μm. A xenon light source provides the illumination for all three modes, which is determined by a filter wheel located in the image processor. Illumination for all three modes of imaging is delivered through the two fiber light guides. In the WL mode, the full visible spectrum (400 to 700 nm) is provided, while in the NBI mode, a filter wheel narrows the spectral bands in the red, green, and blue regime. In the fluorescence mode, a second filter wheel enters the illumination path, and provides fluorescence excitation in the 395 to 475 nm spectral band. In addition, illumination from 525 to 575 nm provides reflected light in the green spectral regime centered at 550 nm. The fluorescence image is collected by the peripherally located CCD detector that has a 490-625 nm band pass filter for blocking the excitation light. Normal mucosa emits bright autofluorescence, thus the composite color appears as bright green. Because the increased vasculature in neoplastic mucosa absorbs autofluorescence, it appears with decreased intensity.

This medical endoscope can be used to collect images after reagent administration and incubation from colon with 1) white light, 2) narrow band, and fluorescence. After entering the colon, a 5 second video is collected and digitized in the white light and narrow band imaging modes. The imaging in this mode is used to assess the spatial extent of the intestinal metaplasia for comprehensive evaluation of polypeptide binding. Then, approximately 3 ml of the fluorescence-labeled peptide is administered topically at a concentration of 10 μM to the colon using a mist spray catheter being careful to cover the full extent of the mucosa. Amounts of reagent of the invention can be determined by one of ordinary skill in the art.

In some embodiments where the detectable label is a radiolabel, the radiolabel is detected by nuclear imaging. Nuclear imaging is understood in the art to be a method of producing images by detecting radiation from different parts of the body after a radioactive tracer material is administered. The images are recorded on computer and on film.

Other methods of the invention involve the acquisition of a tissue sample from a patient. The tissue sample is selected from the group consisting of a tissue or organ of said patient.

Formulations

In various aspects, compositions of the invention are formulated with pharmaceutically acceptable excipients such as carriers, solvents, stabilizers, adjuvants, diluents, etc., depending upon the particular mode of administration and dosage form. The compositions are generally formulated to achieve a physiologically compatible pH, and range from a pH of about 3 to a pH of about 11, about pH 3 to about pH 7, depending on the formulation and route of administration. In alternative embodiments, the pH is adjusted to a range from about pH 5.0 to about pH 8. In various aspects, the compositions comprise a therapeutically effective amount of at least one compound as described herein, together with one or more pharmaceutically acceptable excipients. Optionally, the compositions comprises a combination of the compounds described herein, or may include a second active ingredient useful in the treatment or prevention of bacterial growth (for example and without limitation, anti-bacterial or anti-microbial agents), or may include a combination of reagents of the invention.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol) wetting or emulsifying agents, pH buffering substances, and the like.

EXAMPLES

Figure 1:
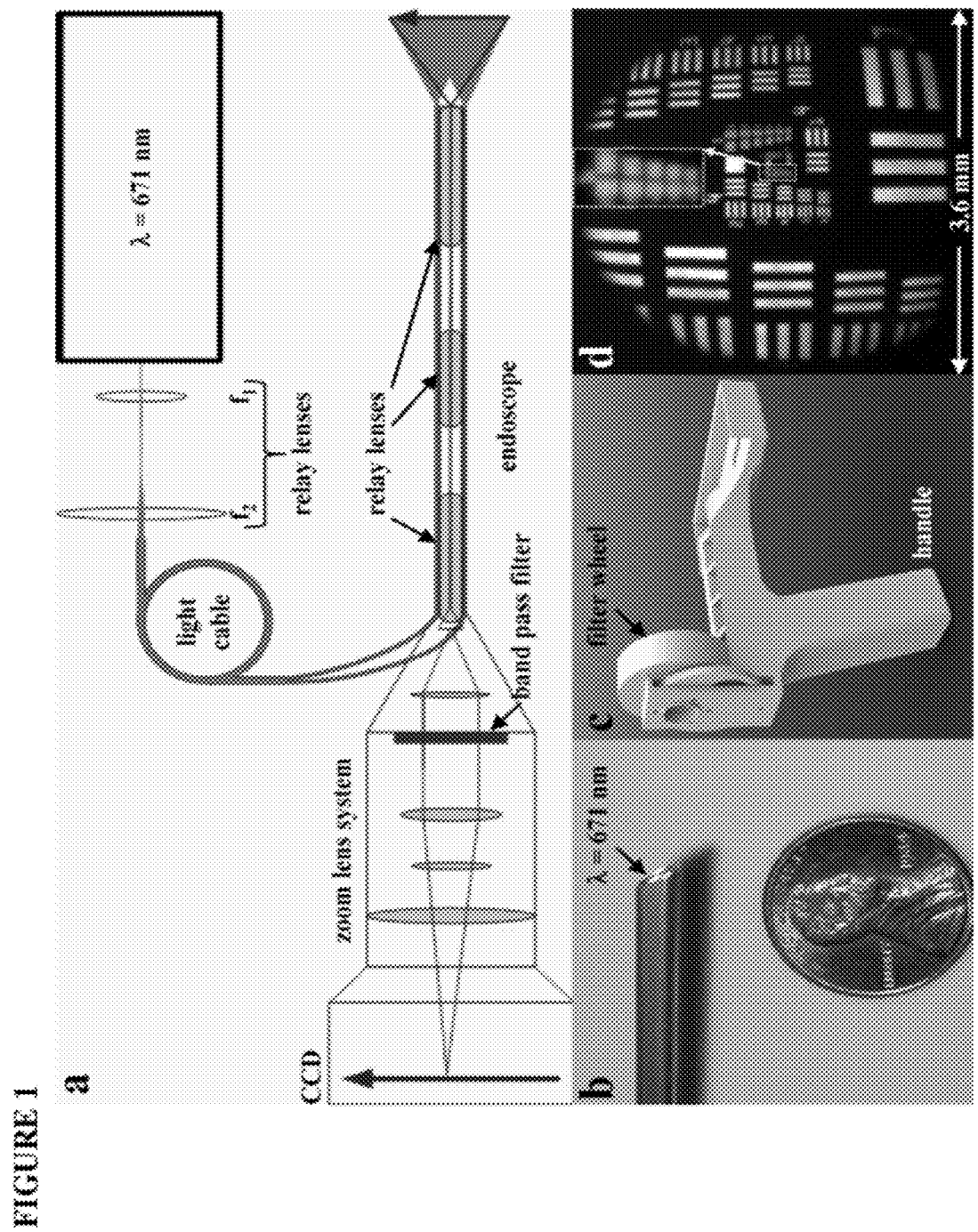
FIG. 1—NIR fluorescence imaging system. a) system schematic, details in text. b) 671 nm excitation is delivered from distal end of (~3 mm diameter) endoscope. c) custom polymer housing contains filter wheel to provide reflectance and fluorescence images. d) image of standard target demonstrates resolution of 9.8 μm and FOV of 3.6 mm at imaging distance of d=2.5 mm.

The invention will be more fully understood by reference to the following examples which detail exemplary embodiments of the invention.

Example 1

Mouse Models

One type of genetically engineered mice (termed CPC: Apc) producing adenomatous polyps, the mice used for peptide screening as described in Example 2 below, are the Cre positive progeny of mice containing Cre recombinase under the control of the Cdx2 promoter (CDX2P-9.5NLS-Cre) and mice with a floxed allele of the Apc gene as described in Hinoi et al., Cancer Res., 67(20): 9721-9730 (2007). This somatic mutation in an Apc allele, which leads to a truncated Apc protein, causes the development of adenomas in the distal colon as early as 10 weeks.

Another type of genetically engineered mice, mice exhibiting hyperplastic colon epithelium (termed Hyperplastic Kras), were generated by breeding mice with mutant Kras allele whose transcription is flanked by LoxP recombination sites with transgenic mice expressing Cre throughout the terminal ileum, cecum and colon (CDX2P9.5-G22Cre). To activate the mutant Kras allele in the mouse intestinal tract, $Kras^{LSL-G12d/+}$ mice were crossed to previously described CDX2p9.5-G22Cre (G22Cre) transgenic mice with mosaic expression of Cre in epithelial cells of the terminal ileum, cecum and colon (Akyol et al., Nature Methods 5, 231-3 (2008).

Mice were cared for under the approval of the University Committee on the Use and Care of Animals, University of Michigan. All mice were housed in specific pathogen-free conditions and supplied water ad libitum throughout the study.

Example 2

Sequences of peptides that bind to dysplastic colon mucosa in the CPC:Apc mice described in Example 1 were identified by phage display and peptides having the sequences were synthesized for further testing.

Phage Display

A T7 library was constructed with the T7Select 10-3b vector as reported in the T7Select System Manual (Novagen, Gibbstown, N.J.). Briefly, random oligonucleotide insert DNA for the X18 library was synthesized as follows: 5'-AAC TGC AAG CTT TTA-(MNN)$_{18}$-ACC ACC ACC AGA ATT CGG ATC CCC GAG CAT-3' (where N represents an equimolar ratio of each nucleotide and M is an equi-molar ratio of adenine and cytosine) (SEQ ID NO: 15). The amino acid translation of the complementary nucleotide sequence is: MLGDPNSGGGX$_{18}$ (SEQ ID NO: 16). The insert DNA was incubated with a complementary extension primer (5'-ATG CTC GGG GAT CCG AAT TCTGGT-3') (SEQ ID NO: 17), Klenow enzyme (New England Biolabs, Beverly, Mass.), and deoxyribonucleotide triphosphates (Novagen) to form the complementary DNA strand. This was digested with EcoR1 and Hindil restriction endonucleases (New England Biolabs). Following phenol/chloroform extraction and ethanol precipitation, the purified fragments were ligated into predigested T7Select 10-3b vector by T4 DNA ligase (Novagen). The ligation reaction was incubated at 16° C., subjected to in vitro packaging, and titered to determine the number of plaque forming units (pfu). The remaining solution was amplified in isopropyl 3-D-1-thiogalactopyranoside (IPTG)-induced BLT5615 until lysis. The lysate was titered and stored at −80° C. in glycerol.

In Vivo Phage Panning Procedure

A 9 month old CPC;Apc mouse was injected via tail vein with 1×10$^{11}$ pfu of the parent T7-18mer library. The library was allowed to circulate for 10 minutes, after which the mouse was euthanized and organs were harvested and kept on ice. The bound phages were recovered by homogenizing each tissue or organ (colon polyps, normal colonic mucosa) (Biogen Pro 200) in DMEM-PI (Dulbecco's Modified Eagle Medium plus protease inhibitors: 1 mM phenylmethanesulfonylfluoride (PMSF), 20 μg/mL aprotinin, and 1 μg/mL leupeptin). The tissue samples were washed 3× with ice-cold washing medium (DMEM-PI containing 1% bovine serum albumin), centrifuging for 5 minutes at 3000 rpm between each wash. After the last wash, freshly starved bacteria were added to each tissue homogenate and incubated for 30 minutes at room temperature (RT). Pre-warmed Luria-Bertani (LB) medium with carbenicillin (50 μg/mL) was then added to the bacteria-homogenate solution and incubated another 30 minutes at RT. The supernatant was recovered after centrifugation and titered to determine the number of bound phage within each tissue tested. This procedure constituted one round of panning. After two rounds of panning, the recovered phage that bound to the colon polyps was cleared twice: once against a homogenized tissue cocktail consisting of colon, kidney, liver and heart and a second time against normal murine colon. A total of four rounds of phage panning were performed, with amplification of the recovered eluate after each panning round. The input phage number (1×10$^{11}$ pfu) was kept constant for each round of panning. The number of phages bound to each organ or tissue was calculated as the output pfu/(input pfu×tissue mass).

After the first two rounds of in vivo panning, the number of phages bound to the colonic adenomas was approximately the same as that for the adjacent normal colon tissue. However, after clearing against normal colon and other organs, the third round showed a 9-fold increase in the number of bound phages to the adenomas over adjacent normal colon tissue. This trend continued after the fourth round of panning. Fifty phages were selected from rounds three and four and the DNA was sequenced. Three entire sequences were repeated twice NGTTSSNNQLINENNIQN (SEQ ID NO: 3), EHMYNTPHTYHTTMKNNK (SEQ ID NO: 4) and QPIHPNNM (SEQ ID NO: 1) (hereafter "Phage 1" or "Peptide 1"), and four partial sequences were repeated twice NKLAAALE (SEQ ID NO: 5), KNYKN (SEQ ID NO: 6), TNTHN (SEQ ID NO: 7) and KHTNN (SEQ ID NO: 8). One of the three repeated phages was less than eighteen amino acids because of the presence of a stop codon within the sequence.

Using the RELIC software, the INFO value for the three candidate phages were calculated against a pool of phages from the initial T7 library [Mandava et al., *Proteomics*, 4: 1439-1460 (2004)]. The INFO scores for the SEQ ID NO: 3 peptide, the SEQ ID NO: 4 peptide, and Peptide 1 were 41.6, 45.2, and 49.1, respectively. A higher INFO score suggests a greater probability that the phage clone identified was not by chance. From this data, the Peptide 1 phage was shown to be the most unique clone of the three and was synthesized for further testing.

Peptide Synthesis

Peptide 1 was synthesized using Fmoc-chemistry by solid phase peptide synthesis according to the literature procedure as described in Fields & Noble, *Int. J. Pept. Protein Res*, 35:161-214 (1990). To ensure the phage and synthetic peptide expressed the same orientation, Peptide 1 was synthesized with 5'-Fluorescein isothiocyanate attached to the amino terminus of the peptide via amino hexanoic acid linker. Deprotection and cleavage of the peptides were achieved by treatment with a cleavage cocktail of trifluoroacetic acid (TFA)/Tri-isopropylsilane/Water (9.5/0.25/0.25/0.25, v/v/v/v) at RT for 3-4 hours. After cleavage of the product from the resin, the peptides were purified by preparative-HPLC using a water (0.1% TFA)-acetonitrile (0.1% TFA) gradient (2-33% acetonitrile over 31 minutes) (Waters Breeze HPLC, Milford, Mass.). The peptides were characterized by an ESI mass spectrometer (Micromass LCT Time-of-Flight mass spectrometer with Electrospray, FITC-Peptide 1 (mass calc. 1451.89, Obs. 1451.7 [M+H]+)). The purity (>95%) of the compound was confirmed by analytical HPLC on a C18 column. As the side chains of amino acids can have significant roles in binding with their receptors, a control peptide containing Gly and Ala (GGGAGGGA) (SEQ ID NO: 18) (hereafter "Control peptide 1"), which does not have any functional groups on the amino acid side chains, was synthesized using same methods [mass (Calc. 1004.08 Obs. 1004.4 [M+H]+)]. All peptides were reconstituted in 1× phosphate buffered saline (PBS) at 500 μM and further diluted in 1×PBS as necessary.

Example 3

The fluorescein-labeled Peptide 1 synthesized in Example 2 was used in endoscopic analysis.

Small Animal Endoscopy and Peptide Administration

Prior to peptide administration, the colon was prepped using a tap water lavage. Using a small animal endoscope (Karl Storz Veterinary Endoscopy, Goleta, Calif.) with an instrument channel for performing biopsy, polyps suitable for peptide administration were located and the colon was rinsed with water until all mucous was removed. FITC-labeled Peptide 1 and Control peptide 1 were delivered in 1×PBS through the instrument channel. The peptides were allowed to incubate for 5 minutes after which the colon was cleansed 3× with a tap water to remove the unbound peptide. Prior to imaging, the colon was inspected for residual peptide solution, and when clean, the colon was insufflated with air and imaged. Fluorescence excitation produced with a 450-475 nm passband filter that can be manually switched to the optical path of a 175 W Nova Xenon light source was delivered to the endoscope via a 3 mm diameter fluid light cable (250 cm length). Fluorescence images were collected with a 510 nm long-pass barrier filter to block the excitation light and detected with a 3-chip color camera with an integrated parfocal zoom lens. Real time video was recorded via firewire connected to a personal computer. Polyps in CPC;Apc mice developing distal colonic adenomas (Peptide 1, n=6 mice, n=18 polyps; Control peptide 1, n=4 mice, n=7 polyps) in addition to Cre recombinase negative littermate controls (Peptide 1, n=2 mice) and Hyperplastic Kras mice (Peptide 1, n=3 mice) were imaged using both white light and fluorescence endoscopy. The CPC;Apc mice imaged using fluorescence endoscopy ranged in age from 3-5 months.

Fluorescent Image Analysis

Videos collected via firewire during endoscopy were exported as .avi video files and converted into sequential .png images using Apple QuickTime. Consecutive white light and fluorescent images for each polyp analyzed were imported into NIH Image J. The white light image was utilized to draw a region of interest (ROI) around the polyp or adjacent normal appearing colonic mucosa which was then superimposed onto the fluorescent image. In experiments herein, a comparison of the difference in the mean findings between two groups was performed using a 2-sided independent samples t-test ($\alpha=0.05$). All data are presented as mean±SD. A p value less than 0.05 was considered as significantly different. Mean grey scale values were calculated for each ROI and a polyp/normal colon, or a target to background ratio (T/B), value was then calculated for each polyp. Target to background ratios were not calculated for Cre recombinase negative littermate control mice or Hyperplastic Kras mice, because these mice were devoid of polyps.

The in vivo endoscopy images revealed that FITC-Peptide 1 bound to the colonic adenomas and provided greater fluorescent signal when compared to the Control peptide 1. Furthermore, FITC-Peptide 1 showed minimal background binding to adjacent colon tissue, also clearly evident during endoscopy. Still, the FITC-Peptide 1 did not bind to colonic mucosa in littermate mice that tested negative for Cre recombinase (control mice without polyps). Furthermore, FITC-Peptide 1 did not show preferential binding to hyperplastic colonic epithelial tissue in the Hyperplastic Kras mouse cohort tested. Lack of binding to the hyperplastic colon epithelium in the Hyperplastic Kras mice, illustrated that Peptide 1 is specific to dysplasic adenomas in the colon. Adenomatous polyps are thought to be precursors to CRC where hyperplastic polyps are not, suggesting that the Peptide 1 could be binding to a cell surface target unique to dysplastic and/or cancerous cells.

Quantitative Analysis

Quantitative analysis of peptide adsorption to distal colonic adenomas revealed FITC-Peptide 1 (T/B: 2.17±0.61) binds 2-fold greater to the colonic adenomas when compared to the FITC-Control peptide 1 (T/B: 1.14±0.15). Independent samples t-test statistical analysis indicated that FITC-Peptide 1 binds in significantly greater amounts to the adenomas than FITC-Control peptide 1, $p<001$. T/B calculations for the FITC-Peptide 1 binding to the control mice was not possible, because an average grey scale value could only be obtained for the adjacent normal tissue.

Confocal Fluorescence Imaging

Preferential binding of Peptide compared to the Control peptide 1 on the adenomatous polyps was confirmed with confocal microscopy. A polyp biopsy was taken after 5'-FITC-labeled peptide administration in vivo, incubated in 1 µg/mL Hoechst dye for 5 minutes to stain living nuclei, rinsed 3× with 1×PBS and imaged on a Leica Confocal Microscope (Leica Microsystems, Bannockburn, Ill.).

Confocal microscopy images of biopsied polyps collected subsequent to peptide administration showed evidence that Peptide 1 bound more to adenomas than the Control peptide 1.

Example 4

Binding of peptides to excised polyps was also tested.
Ex Vivo Peptide Binding

Polyps from CPC;Apc mice (n=3 mice, 5 polyp pairs) were excised and washed 3× in PBS. The polyps were incubated in 100 µM peptide solution for 5 minutes and subsequently washed 3× with 1×PBS. Polyps were grossly imaged using the small animal endoscope to view binding to the polyp as a whole. Pairs of polyps (one candidate, one control) were imaged at a time to allow for the calculation of a candidate peptide to Control peptide 1 binding ratio for each pair analyzed. An average binding ratio was calculated ± one standard deviation. A similar procedure to determine mean grey scale values for image analysis was followed for the ex vivo polyps as described above for the in vivo polyps.

This study showed a similar 2-fold increase in binding of Peptide 1 compared to the Control peptide 1.

Confocal Fluorescence Imaging of Ex Vivo Binding

Preferential binding of the Peptide 1 compared to the Control peptide 1 on the adenomatous polyps was again confirmed with confocal microscopy. After peptide incubation, excised polyps were incubated ex vivo in 1 µg/mL Hoechst dye for 5 min to stain living nuclei, rinsed 3× with 1×PBS and imaged on an Olympus Confocal Microscope (Olympus, Tokyo, Japan).

Peptide 1 displayed enhanced binding to whole polyps ex vivo. Gross analysis of peptide binding revealed that the FITC-Peptide 1 bound to the excised polyps in greater quantity than the FITC-Control peptide 1. Comparison of between FITC-Peptide 1 and FITC-Control peptide 1 binding showed Peptide 1 bound 2.51±0.59 times greater than the Control peptide 1 for the whole polyp pairs analyzed.

From the ex vivo peptide binding experiment, confocal microscopic imaging revealed that the FITC-Peptide 1 showed increased binding to the dysplastic crypts when compared to the FITC-Control peptide 1. When the Hoechst nuclear stain is overlaid with the FITC-labeled peptide binding, it is evident that the Peptide 1 is binding dysplastic colonocytes. Minimal to no binding was found for the FITC-Control peptide 1.

Example 5

Histological examination of the polyps from phage panning, in vivo peptide administration, ex vivo peptide administration, and biopsies was performed.
Histology Polyps were fixed in phosphate-buffered formalin for 24 hours, paraffin-embedded and sectioned into 10 µm thin slices and stained with hematoxylin and eosin. Histological images were captured using an Axioskop2 upright microscope (Carl Zeiss, Inc.).

Histology of the all polyps showed dysplasia, characterized by enlarged nuclei, hyperchromaticity, and distorted crypts.

Example 6

Experiments were carried out to determine binding of the synthetic peptides to human surgical specimens of colon cancer. In brief, frozen or fixed non-neoplastic or neoplastic human colon tissue sections were cut with 10 µM thickness. The fixed sections were heated at 60° C. to melt out the wax followed by deparaffinization with xylene and ethanol. The antigen retrieval was performed using Tris-EDTA buffer (10 mM Tris base, 1 mM EDTA, 0.05% Tween-20, pH 9.0) at 95° C. for 10 min. The sections were then washed with PBS (1×) and used for further staining. The fresh frozen sections were used directly after cut without any further process to localize peptide binding. The sectioned tissues were air dried and washed with PBS 1×. Sections were incubated with FITC labeled peptides (10 µM) for 15 min at RT. The sections were washed three times each for 1 min in PBS and fixed with 4% paraformaldehyde for 10 min. After fixing, the sections were washed again (1×) and mounted with ProLong® Gold reagent with DAPI (Invitrogen, Carlsbad, Calif.). The sections were imaged under a confocal microscope (Leica Microsystems GMBH, Wetzlar, 35578 Germany). All surgical specimens were obtained from the tissue procurement core of University of Michigan with approval from the Institutional Review Board (IRB).

Example 7

Sequences of peptides that bind to a human colorectal adenocarcinoma cell line were identified by phage display and peptides having the sequences were synthesized for further testing.

Cell Lines and Cultures

The human colorectal adenocarcinoma cell line HT29 and non-malignant intestinal cell line Hs738.St/Int. were obtained from the American Type Culture Collection (ATCC, Manassas, Va.). The HT29 cells were cultured in McCoy's medium (Gibco, Calif., USA) containing 10% fetal bovine serum (FBS, Gibco, Calif., USA) and 1% penicillin/streptomycin (Invitrogen Corp. USA). The Hs738.St/Int. cells were cultured in DMEM (Gibco, Calif., USA) containing 10% FBS, 1% penicillin/streptomycin and 1% glutamax. Both cell lines were cultured at 37 deg C. in 5% $CO_2$. The cells were passaged using 0.25% EDTA containing trypsin (Mediatech Inc. Manssas, Va.).

In Vitro Panning Procedure

Peptide selection was performed using a technique of phage display (Ph.D.-7, New England Biolabs, Beverly, Mass.) and a biopanning strategy based on a subtractive whole-cell approach Kelly, et al. Cancer Res. 64: 6247-6251 (2004); and Zhao et al., Clin Cancer Res 13: 6049-5055 (2007). HT29 and Hs738.St/Int. cells were grown to log-phase, detached either with cell dissociation buffer (Invitrogen, Carlsbad, Calif.) or Trypsin with 0.25% EDTA (Mediatech Inc. Mansas, Va.) and immersed in blocking buffer, PBS with 1% bovine serum albumin (BSA), for 30 min at 4° C. with continuous agitation. Three rounds of clearing were performed by incubating ~$10^6$ Hs738.St/Int. cells with a total of ~$10^9$ plaque-forming units (pfu) of the phage library for 30 min at 4° C. The cleared phage in the supernatant was amplified and titered with E. coli (ER 2738). The amplified titer ($2 \times 10^{11}$) was used for further positive selection against HT29 cells (~$10^7$) in PBS containing 0.2% Tween-20 (PBST) for 60 min at 4° C. The cells were washed three times with cold PBST. The bound phage were then eluted with 1 mL of 0.2 M glycine (pH 2.2) containing 0.1% BSA for 8 min, and immediately neutralized with 150 µL of 1 M Tris (pH 9.2). The eluted phage was amplified, precipitated and titered according to manufacturer instructions. The resulting phage ($2 \times 10^{11}$ pfu) was used to perform further 4 additional rounds of biopanning for positive selection against the HT29 cells, to enrich the pool of candidate phage. After three rounds of in vitro panning, 60 plaques were randomly selected and their sequences were analyzed with an ABI Automatic DNA Analyzer. A primer 5'-CCC TCATAG TTA GCG TAA CG-3' (SEQ ID NO: 19) (-96 gIII sequencing primer, provided in the phage display peptide library kit, New England Biolabs) corresponding to the pIII gene sequence of the M13 phage was used for sequencing.

Preferential binding of the candidate phage to target cells was validated by bound phage counts. The candidate phages and non-insert wild-type (WT) phage (M13KE, New England Biolabs, Beverly, Mass.) were amplified, precipitated and titered per manufacturer's instruction. HT29 and Hs738.St/Int. (~$5 \times 10^6$) cells were grown to log-phase, detached, and blocked, as described above. A total of $2 \times 10^{11}$ pfu of either the candidate or wild-type phages were incubated with these cells for 15 min with continuous gentle agitation at room temperature. After three rounds of washing with PBS/0.2% Tween-20, the bound phages were eluted from the cells with 0.2 M glycine (pH 2.2) containing 0.1% BSA buffer for 8 min and titered with E. coli. The number of plaques was counted, and the number of candidate phages that bound to the target cells was compared with that found for the non-target cells and for no-insert wild type phage.

After five rounds of positive selection with HT29 and three rounds of negative selection with Hs738.St/Int. cells, the candidate phage pool was enriched by 78 fold [$10 \times 10^2$/µl (first round) vs. $78 \times 10^3$/µl ($5^{th}$ round)] in $5^{th}$ round in comparison to first round, which indicates the enough specificity of phage pool for HT29 cells. A total of 60 clones from $5^{th}$ rounds yielded the following amino acid sequences multiple times: SILPYPY (SEQ ID NO: 9) (4 times), KCCFPAQ (SEQ ID NO: 2) (hereafter "Peptide 2" or "Peptide 2 phage") (13 times), YRAPWPP (SEQ ID NO: 10) (3 times), QPWPTSI (SEQ ID NO: 11) (3 times), WPTPPYA (SEQ ID NO: 12) (1 time), MHAPPFY (SEQ ID NO: 13) (1 time), VRPTLPM (SEQ ID NO: 22) (2 times) and NFMESLPRLGMH (SEQ ID NO: 23) (4 times). Multiple sequence alignment analysis did not reveal any strong homology among these repeated sequences. Only some short motifs such as PP, FP and WP were found. These sequences were further tested with HT29 and Hs738.St/Int. cell lines and bound phages were recovered in triplicate and titered with E. coli ER 2738. The Peptide 2 phage bound with the HT29 cell displayed 7-fold higher binding as compared to Hs738.St/Int. (4293333±279886 Ht29 vs. 682323±59013 Hs738.St/Int.) and 145 times (29666±2516 wt) than non-insert wild type phage with P value<0.001. This result indicates that the Peptide 2 phage binds with high specificity to the HT29 cells.

Based on this result, the Peptide 2 phage and a synthetic peptide corresponding to the Peptide 2 amino acid sequence were used for further studies. The sequences of this peptide were analyzed with the National Center of Biotechnology Information BLAST (Basic Local Alignment Search Tool). While complete homology for the entire sequence was not found, this peptide does have partial homology to the ubiquitin protein ligases (5 of 7 amino acids, /KCCFP) (SEQ ID NO: 20), which is involved in tumor generation, development and metastasis in gastric, colonic and liver tumors by ubiquitin-proteasome pathway. Mani, et al., Cancer; J Clin Oncol, 23:4776-4789 (2005); Voutsadakis, Biochim Biophys Acta, 1782:800-808 (2008).

Cell-Based ELISA with Phage

Preferential binding of the Peptide 2 phage to HT29 cells was also validated by cell based ELISA. HT29 and Hs738.St/Int. ($2 \times 10^5$) cells were detached and blocked as mentioned above and incubated with $2 \times 10^{11}$ pfu of either the Peptide 2 or wild-type phage for 20 min at RT in triplicate. After washing 3 times with PBS/0.2% Tween-20, cells were incubated with anti-M13 antibody (IgG) conjugated to horseradish peroxidase (HRP, 1:2000 dil.) (Amersham, Piscataway, N.J.) for 60 min at RT with continuous agitation. After washing 2 times with PBST; tetramethylbenzidine (TMB) substrate (Sigma, Saint Louis, Mo.) was added to the cells and color was developed for 3 min at RT. The reaction was quenched with the 1N $H_2SO4$ and incubated further for 30 min to observe the final end point at RT. The optical density (absorbance) was measured at 450 nm. Untreated cells with phages were used as controls and subtracted from the binding with Peptide 2 phage.

Results indicated that Peptide 2 phage clone could bind effectively to HT29 cell compared with Hs738.St/Int. and non-insert wild type phage by 5 fold and p-value<0.002.

Synthesis of Peptides

Peptide 2 peptide and a control peptide GGGAGG-GAGGGK (FITC)-NH2 (SEQ ID NO: 21) (hereafter "Control peptide 2") were synthesized by solid phase synthesis with Fmoc chemistry. Fmoc protected L-amino acids were used and synthesis was assembled on rink amide MBHA resin using PS3 (Protein Technologies, Inc. AZ) automatic peptide synthesizer. The FITC was labeled at the C-terminus on the side chain of lysine residue via GGGSK linker (SEQ ID NO: 14). The glycine residues provide a spacer function which prevents stearic hindrance between the binding motif and fluorescent label. Also, the linker residue provides the same orientation of the peptide relative to the fluorescence label as that for the phage. Moreover, this spacer has the same amino acid sequence as that on the pIII coat protein of the M13 bacteriophage. Control peptide 2 was designed with multiple glycines and alanines to have different structure and properties in terms of net charge and side chains and with the same number of amino acids as that for the target peptide.

Unlabeled peptides were also synthesized for a competitive binding study. Cleavage of the peptides from the resin was achieved by treatment with a mixture of 3 mL TFA:TIS:H2O (95:2.5:2.5 v/v/v) at RT for 4 hr (Sigma Aldrich, St. Louis, Mo.). After filtration and washing of the resin by TFA, a gentle stream of nitrogen was used to remove the excess TFA. The crude peptide was triturated with diethyl ether chilled at −20° C. and then centrifuged at 3,000 rpm for 10 min at 4° C. The crude product was purified by prep-HPLC with a C18 column (Waters, city, state) using a water (0.1% TFA)-acetonitrile (0.1% TFA) gradient to give sufficient amount of the desired products. The successful synthesis was confirmed by LC/ESI mass spectrometry (Platform II, micromass, Manchester, UK) and its homogeneity (>95%) was confirmed by reverse phase analytical HPLC (2489 Breeze system, Waters Inc, MA) using a C18 column.

Example 8

Binding of FITC-Peptide 2 to target cells was validated in multiple experiments.
Flow Cytometry Analysis Preferential binding of FITC-Peptide 2 to target cells was validated using flow cytometry. HT29 and Hs738.St/Int. (~2×$10^5$) cells were grown, detached, and blocked as described above. These cells were incubated with the FITC-Peptide 2 or -Control peptide 2 (10 µM) for 60 min at 4° C. with continuous agitation. The cells were then washed (3×) with cold PBST followed by immediate fixing for 10 min. with 4% paraformaldehyde. The cells were washed again (1×) with PBS and resuspended in 1 mL of PBS. Flow cytometry was performed using FACSDiVa (BD® LSRII, BD Biosciences, San Jose, Calif.) and analyzed using Flowjo analysis program (Tree Star Inc., Ashland, Oreg.).

About 97% of the total HT29 cell population was bound with FITC-Peptide 2 when gated for positive binding through FITC channel compared to 18.6% for FITC-Control peptide 2. Furthermore, both the FITC-Peptide 2 and FITC-Control peptide 2 bound minimally to the Hs738.St/Int cells.
Fluorescence Microscopy Preferential binding of the FITC-Peptide 2 and FITC-Control peptide 2 to target and non-target cells was also validated via fluorescence microscopy. HT29 and Hs738.St/Int. cells were grown in 22 mm2 cover slips with ~80% confluence. Blocking of non-specific binding was performed by adding PBS/0.5% BSA for 30 min. The cells were then incubated with 10 µM of FITC-Peptide 2 or FITC-Control peptide 2 either at 4 or 37° C. for 15 min followed by 1 µg/mL Hoechst dye (Sigma Aldrich, St. Louis, Mo.) along with the peptide. The cells were washed with PBS for 3 times and fixed with 4% paraformaldehyde at room temperature for 10 min. After fixation, the cells were washed again with PBS (1×) and mounted with ProLong® Gold reagent (Invitrogen, Carlsbad, Calif.) and the fluorescence images were acquired with Leica Confocal system. (Leica Microsystems GMBH, Wetzlar, 35578 Germany)

FITC-Peptide 2 binds to the surface of the HT29 but not the surface of the Hs738.St/Int cells. As expected, FITC-Control peptide 2 did not bind to either the target or control cells.

In addition, the ability of the FITC-Peptide 2 peptide to internalize within the HT29 cells was tested. HT29 cells were incubated for 15 min. at either 4° C. or 37° C. in the presence of 10 µM FITC-Peptide 2. When HT29 cells were incubated with FITC-Peptide 2 peptide at 4° C., most of the peptide binding appears to be confined to the cell surface as revealed by the overlay image stained with 4',6-diamidino-2-phenylindole. The spatial extent of the cell nuclei showed affinity binding of FITC-Peptide 2 to the plasma membrane of the HT29 cells. In contrast, incubating HT29 cells with FITC-Peptide 2 at 37° C. revealed the presence of diffuse staining throughout the cells.
Determination of Binding Constant The binding affinity of FITC-Peptide 2 to HT29 cells ($1 \times 10^5$) was determined using various concentrations of the peptide. The fluorescence intensity of the peptide bound to the HT29 cells was measured at saturation. Then, the FITC-labeled peptide was serially diluted in PBS at concentrations that varied from 0 to 70 µmol/L and incubated with $1 \times 10^5$ HT29 cells at 4° C. for 1 hr. After washing 3 times with cold PBS/0.2% Tween 20 solution, the unbound peptide was rinsed off. The cells were resuspended in 200 µL PBS and transferred to a 96 well plate. The fluorescence intensity I was measured at 525 nm using 485 nm as the excitation wavelength on a multi-well plate reader (CytoFluor Series 4000; Applied Biosystems Inc, Foster City, Calif.). Binding of the peptide to the cells was calculated using the peptide emission intensity with the same concentration without the cells present. The peptide equilibrium dissociation constant $K_d=1/K_a$ was calculated by performing a least squares fit of the data to the non-linear equation $I=(I_0+I_{max}K_a[X])/(I_0+K_a[X])$. $I_0$ and $I_{max}$ are the initial and maximum fluorescence intensities, corresponding to no peptide and at saturation, respectively, and [X] represents the concentration of the bound peptide. Origin 6.1 data analysis software (Origin Lab Corp, Northampton, Mass.) was used to fit the equation for non-linear least square fitting.

With respect to the relative fluorescence intensity at 525 nm as a function of the concentration of the FITC-Peptide 2 bound to the HT29 cells, a non-linear increase in intensity until it reaches to the saturation was fitted with the equation and yielded the $K_d$ value of 65 nM/L ($R^2=0.988$).

Example 9

Binding of Peptide 2 phage as well as Peptide 2 itself to human colon tissue was examined.
Immunohistochemistry with Phage Frozen or fixed non-neoplastic or neoplastic human colon tissue sections were cut with 10 µM thickness. The fixed sections were heated at 60° C. to melt out the wax followed by deparaffinization with xylene and ethanol. The antigen retrieval was performed using Tris-EDTA buffer (10 mM Tris base, 1 mM EDTA, 0.05% Tween-20, pH 9.0) at 95° C. for 10 min. Then the sections were washed with PBS (1×) and used for further staining. The fresh frozen sections were used directly without further processing. The sections were air-dried on slides, rinsed twice with PBS and then fixed with 4% paraformaldehyde for 10 min. The sections were rinsed-off with PBS and blocked with 1% BSA for one hour at RT. Tissue sections were stained with hematoxylin following the standard protocol for localizing the nucleus. Then, sections were incubated with targeted phages or non-insert wild type phages ($2 \times 10^{11}$ pfu) for 15 min at RT. Slides were then rinsed 3 times with PBS for 1 min each and blocked for 10 min with 3% hydrogen peroxide. Slides were again rinsed 2 times for 1 min each with PBS, and staining with HRP-conjugated anti-M13 monoclonal phage antibody (1:200 dilutions) for 1 hr at RT. Slides were rinsed 2 times for 1 min each with PBS and developed with diaminobenzidine; DAB (Sigma, St Louis, Mo.) solution for 3 min. Finally, slides were rinsed in PBST 3 times for 1 min each and imaged under a fluorescence microscope (Carl Zeiss MicroImaging GmbH, Gottingen, Germany). The non-insert wild type and only HRP stained sections were used as negative controls.

To correlate the binding of Peptide 2 phage between diseased and healthy tissue sections, H & E staining from the serial sections was also assessed for diagnosis. The frozen sections of human specimens were fixed with 4% paraformaldehyde for 10 min at RT. Then the sections were stained with H&E following the standard protocol. Histopathologic interpretation of each section was performed by a gastrointestinal pathologist (HA) and classified as (1) normal mucosa, (2) dysplasia and (3) adenocarcinoma for comparison with the average fluorescence intensity from the serial sections.

The Peptide 2 phage was found to localize in dysplastic adenomas and carcinoma sections, that stained dark brown distinctly, indicated the positive binding region of the phage to these pre-malignant and malignant lesions. The dysplastic adenoma and carcinoma tissue sections stained with insert less wild type phage clone showed negative staining. The normal colonic mucosa did not stain either with Peptide 2 or with insert less phage. It is thus clear that Peptide 2 phage was able to bind specifically to adenoma and carcinoma cells. The representative H & E sections are shown as gold standard for comparison with staining.

Binding of Synthetic Peptides to Human Surgical Specimens of Colon Cancer

Fresh frozen sections from human surgical specimens were cryosectioned with 10 μM thickness and used to localize peptide binding. The sectioned tissues were air dried and washed with PBS 1×. Sections were incubated with FITC labeled peptides (10 μM) for 15 min at RT. The sections were washed three times each for 1 min in PBS and fixed with 4% paraformaldehyde for 10 min. After fixing, the sections were washed again (1×) and mounted with ProLong® Gold reagent with DAPI (Invitrogen, Carlsbad, Calif.). The sections were imaged under a confocal microscope (Leica model no, city, state). All surgical specimens were obtained from the tissue procurement core of University of Michigan with approval from the Institutional Review Board (IRB).

FITC-Peptide 2 differentially stained the surgical specimens from human colon adenocarcinoma as opposed to normal colonic mucosa. FITC-Peptide 2 stained consistently with pre-malignant lesions (dysplastic adenomas, n=4) and malignant lesions (carcinoma, n=6) from 10 different patients; whereas, no binding was observed the normal mucosa (n=10). FITC-Control peptide 2 was not able to bind with any of the specimens classified from normal to carcinoma. The representative H and E sections are shown as gold standard for comparison with staining. Statistical evaluation indicated that the FITC-Peptide 2 binds more strongly with carcinoma (T/B=7) compared to normal mucosa and 1.5-fold higher than dysplastic adenomas. The T/B ratio for FITC-Peptide 2 vs. FITC-Control peptide 2 was 6, 3 and 1 for carcinoma, adenoma and normal mucosa respectively. These results suggested that Peptide 2 binds avidly with pre-malignant and malignant lesions of colonic neoplasia.

Example 10

This example describes the design, construction, and validation of a near-infrared (NIR) labeled peptide and matching wide-field instrument with sub-cellular resolution that were used to visualize individual pre-malignant (dysplastic) crypts in real time in vivo. This methodology can be used longitudinally to evaluate molecular expression in small animal models, and can also be directly translated into the clinic for early cancer detection.

NIR-Labeled Fluorescent Peptides

Octapeptide QPIHPNNM (Peptide 1; SEQ ID NO: 1) was conjugated with Cy5.5 (Lumiprobe, LLC, Hallandale Beach, Fla.) on the N-terminus via an amino-hexanoic acid linker using NHS activation chemistry. The peptide was prepared using solid-phase synthesis by applying standard Fmoc chemistry on Rink amide MBHA amide resin (Anaspec, Calif.). Cy5.5-NHS ester was conjugated to the N-terminus of the peptide in mixed DCM/DMF (1:3) at pH 9 adjusted with diisopropylethylamine (DIEA) overnight. Side-chain protecting groups were removed with a mixture containing trifluoroacetic acid (TFA)/triisopropylsilane (TIS)/water (95:2.5:2.5, V/V/V). The crude product was purified using semi-preparative HPLC(C-18, Waters) with water-acetonitrile gradient mobile phase containing 0.1% TFA. The products were analyzed with HPLC System (Waters Breeze, 2489) using a C-18 analytical column and Q-TOF mass spectrometer (Agilent Technologies, Inc.; Santa Clara Calif.). To investigate the specificity of the target peptide, an unrelated peptide YTTNKH (SEQ ID NO: 27) was selected randomly for use as a control. This peptide was synthesized, labeled with Cy5.5, purified and analyzed.

On mass spec, the experimental m/z (mass units) measured for the peptides were found to agree with their expected molecular masses: QPI-Cy5.5, expected=1668.91 and experimental=1668.91; YTT-Cy5.5, expected=1755.95 and experimental=1756.8, respectively. The purity of the final synthesized products was >95% each. The peak fluorescence emission occurs at $\lambda_{em}$=709 nm and 708 nm for QPI-Cy5.5 and YTT-Cy5.5, respectively, at a concentration of 10 μM in 1×PBS, and has a spectral range of approximately 680 to 900 nm.

Specificity of the Conjugated Peptide for Human Colonic Neoplasia

All specimens were obtained with approval from the University of Michigan Institutional Review Board (IRB). Freshly resected specimens of human colonic mucosa were frozen in OCT and sectioned with 10 μm thickness using Microm-HM-550 Microtome (EquipNet, Inc. Canton, Mass.). The sections were then air dried, washed with PBS 1×, and incubated with the Cy5.5-labeled peptides at a concentration of 10 μM for 15 min at RT. The sections were washed 3× for 1 min in PBS and fixed with 4% paraformaldehyde for 10 min. After fixation, the sections were washed again (1×) and mounted with ProLong Gold reagent with DAPI (Invitrogen, Carlsbad, Calif.). The sections were imaged under a confocal microscope (Leica TCS SP5 Microsystems, Bannockburn, Ill.). Adjacent sections were sent for routine histology. The average intensity from the entire field-of-view of each image was calculated using Matlab (Mathworks, Natick, Mass.).

For the ex-vivo peptide immunohistochemistry, the nonparametric Kruskal-Wallis test was used to determine if observed differences are statistically significant among all three pathological classifications. The nonparametric Mann-Whitney test was used for comparisons between two independent samples, and differences with p<0.05 were considered significant.

Figure 2A:
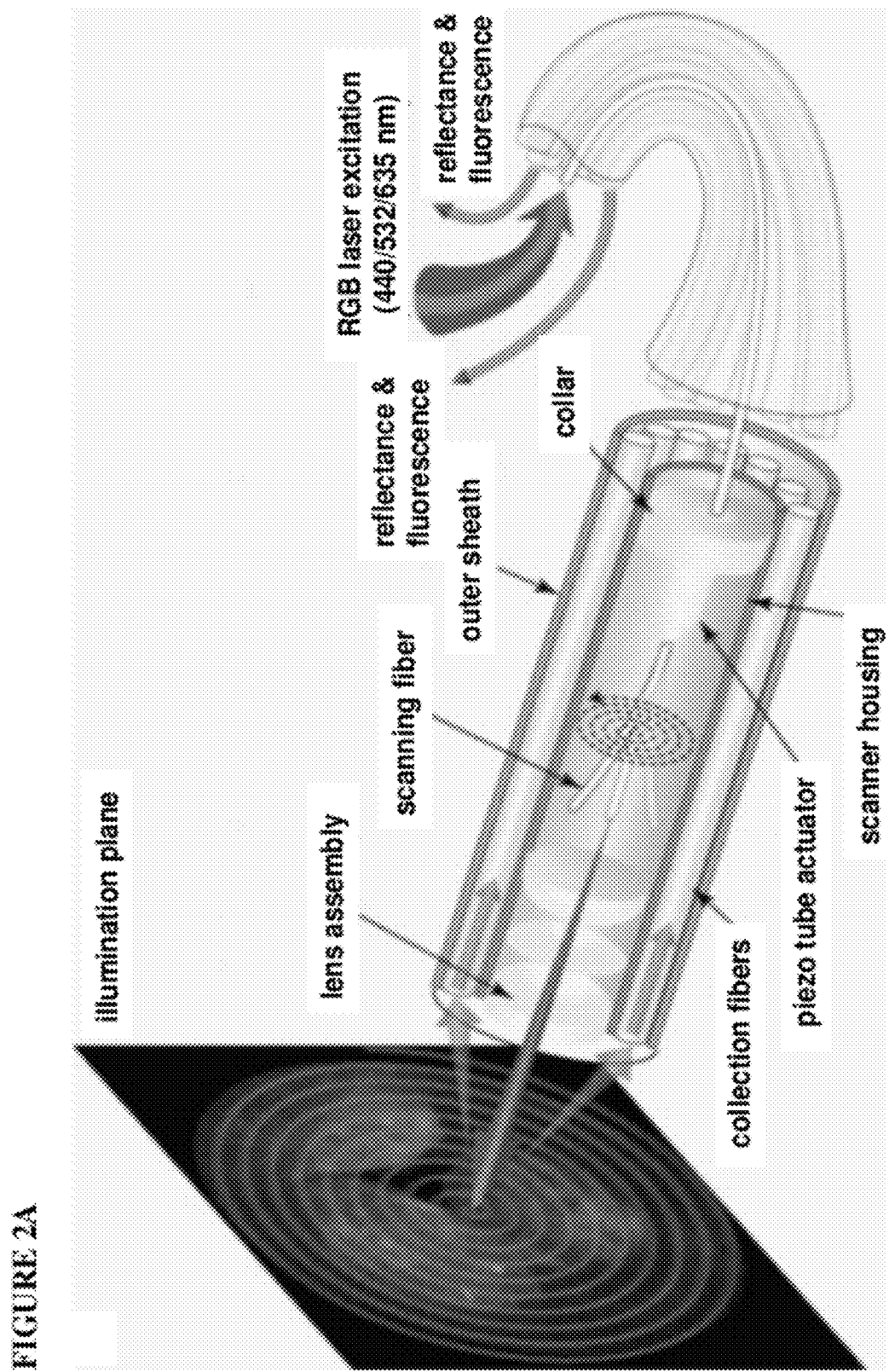
FIG. 2—Multi-spectral scanning fiber endoscope. A) Optical design. RGB laser excitation (440, 532, and 635 nm) is delivered into a single-mode optical fiber that is scanned in a spiral pattern by a piezo tube actuator and focused onto the tissue (illumination plane) by a lens assembly. Fluorescence is collected by a ring of 12 collection fibers mounted around the periphery of the scanner housing, protected by an outer sheath. B) Fluorescence detection. Reflectance from RGB laser excitation is removed using a combination of long pass ($\lambda_{LP}$=450 nm) and notch ($\lambda_{N1}$=532 nm and $\lambda_{N2}$=632.8 nm) filters. Fluorescence is deflected into individual RGB channels using dichroic minors DM1 ($\lambda_c$=460 nm) and DM2 ($\lambda_c$=550 nm) and an additive dichroic filter set ($\lambda_R$, $\lambda_G$, and $\lambda_B$) prior to detection with PMTs.
Figure 2B:
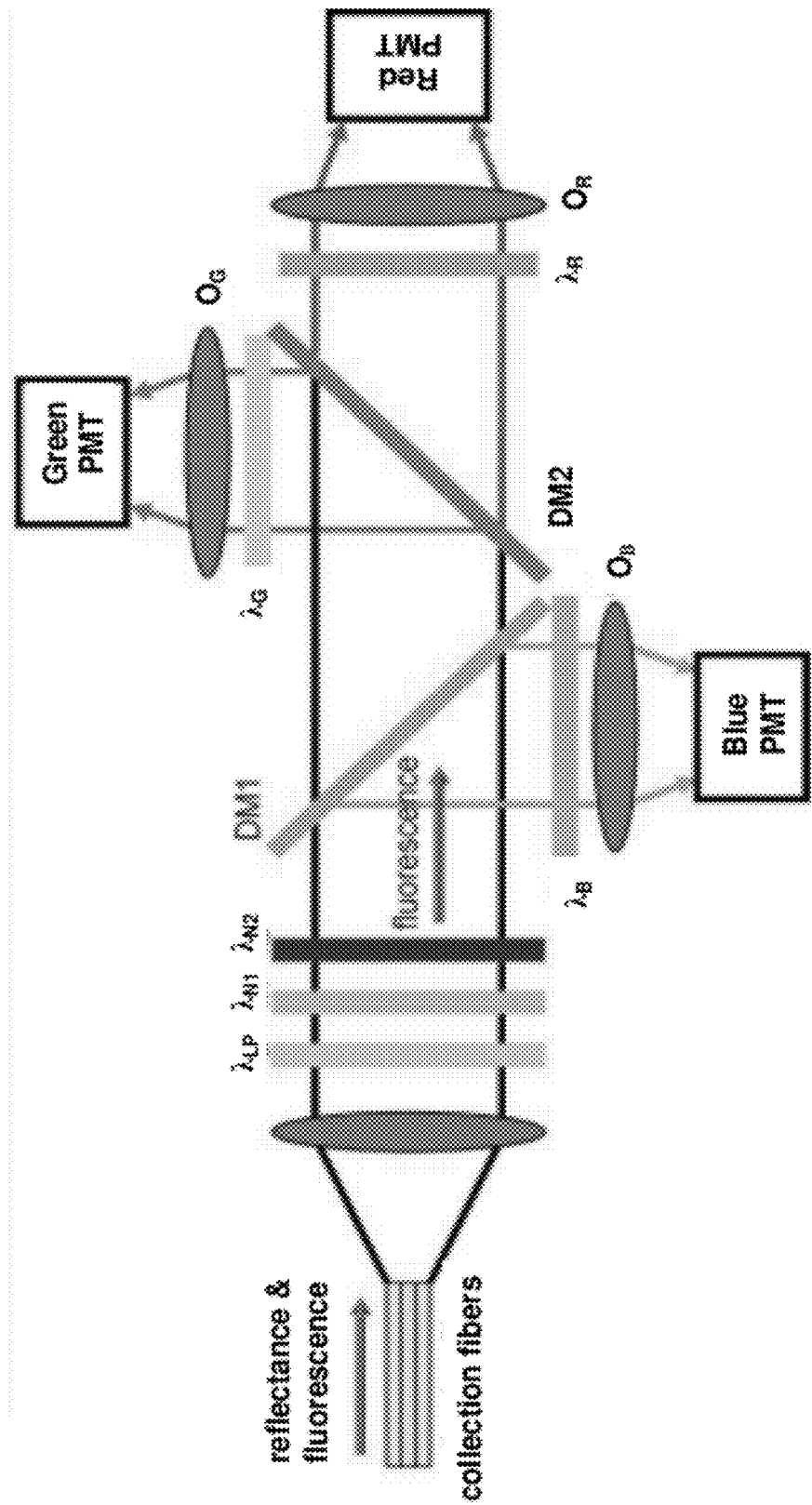

The QPI-CY5.5 peptide demonstrated no binding to normal colonic mucosa (n=7), but consistently stained dysplasia (n=8), shown in Supplementary FIG. 2B, and adenocarcinoma (n=10). The YTT-Cy5.5 (control) peptide did not stain any of the specimens, including normal, dysplasia, and adenocarcinoma. In total, the QPI-Cy5.5 peptide was found to selectively stain dysplasia in 6/8 and adenocarcinoma in 8/10 sections of human specimens. The QPI-Cy5.5 peptide did not stain any of the 7 sections of normal colonic mucosa. YTT-Cy5.5 did not stain either normal or dysplasia, and was found to bind minimally to 5/10 adenocarcinoma sections. The mean NIR fluorescence intensities on immunohistochemistry for QPI-Cy5.5 peptide binding to normal, dysplasia and adenocarcinoma were 1.5±1.0, 10.7±3.3 and 9.8±2.4 AU, respectively. The resulting intensity ratio for dysplasia and adenocarcinoma was 7.1 (p<0.0049) and 6.5 (p<0.0168) relative to that for normal colonic mucosa. A comparison of the mean fluorescence intensities between dysplasia and adenocarcinoma using QPI-Cy5.5 peptide was not significantly different, p<0.41. The T/B ratio for binding by the QPI-Cy5.5 peptide in comparison to the YTT-Cy5.5 peptide was 26.7, 2.9, and 1.8 for dysplasia, adenocarcinoma and normal mucosa, respectively. The average T/B ratio for QPI-Cy5.5 was 3.42±1.30 and that for YTT-Cy5.5 was 1.88±0.38. Non-parametric Mann-Whitney independent samples analysis showed that the fluorescence intensity associated with binding of the target peptide to dysplasia was greater than that of the control with significance, p=0.007.

NIR Fluorescence Imaging System

A schematic of the NIR endoscopic imaging system is shown in FIG. 1a. The distal end of the endoscope is ~3 mm in diameter, and delivers excitation at $\lambda_{ex}$=671 nm (FIG. 1b). A custom polymer housing contains a filter wheel to provide both reflectance and fluorescence images, and has a handle for holding the instrument (FIG. 1c). Using a standard target, a resolution of 9.8 μm (group 6, element 5) was measured at a distance of 2.5 mm, a typical dimension used for in vivo imaging, resulting in a FOV with diameter of 3.6 mm (FIG. 1d). A diode-pumped solid state laser (TechnicaLaser Inc, Winter Park, Fla.) with $\lambda_{ex}$=671 nm is used to excite the Cy5.5 labeled peptides. The intensity is tunable over a range from 1 to 100 mW. The incident beam is expanded to 3 mm in diameter by a pair of relay lenses with focal lengths of $f_1$=30 and $f_2$=50 mm (Thorlabs Ltd., Newton, N.J.) to fill the aperture of a fluid light cable that is coupled to a Hopkins® II rigid endocope (Karl Storz, Goleta, Calif.). This pediatric urethroscope (Karl Storz Veterinary Endoscopy, Goleta, Calif.) has a ~3 mm outer diameter and a 3 Fr instrument channel. Fluorescence images collected by the endoscope are transmitted by a set of relay lenses onto a CCD detector that has dimensions of 8.7×6.9 mm$^2$ and 1388×1040 pixels (Carl Zeiss MicroImaging, LLC, Thornwood, N.Y.). A zoom lens system (NT58-440, Edmund Optics Inc., Barrington, N.J.) with a tunable focal length of 20-100 mm, F#1.6-16 aperture was used to magnify the image to fill the dimensions of the CCD. The resolution of this system was measured using a standard target (USAF-1951, Newport Corporation, Irvine, Calif.). Each frame was collected in 100 ms (10 Hz), and transferred to the computer by firewire. The optics and detector were contained within a custom housing made of light weight polymer. A filter wheel was incorporated into the handle of the housing to quickly switch between collection of reflectance and fluorescence images. A band pass filter that transmits NIR fluorescence from $\lambda_{em}$=696 to 736 nm (FF01-716/40-25, Semrock, Inc., Rochester, N.Y.) was used.

CPC;Apc Mouse Model of Colonic Dysplasia

Mice were cared for under the approval of the University Committee on the Use and Care of Animals (UCUCA) at the University of Michigan. The CPC;Apc mice are genetically engineered with a Cre recombinase under the control of the Cdx2 promoter (CDX2P-9.5NLS-Cre) and a floxed allele of the APC gene. This Cre-regulated somatic mutation in one of the Apc alleles causes dysplasia to develop spontaneously in the distal colon of the mouse, allowing for minimally invasive imaging to be performed. All mice were housed in specific pathogen-free conditions and supplied water ad libitum throughout the study. Animals ranged in age from 6 to 9 months.

In Vivo NIR Fluorescence Imaging

Anesthesia was induced and maintained with inhaled isofluorane mixed with oxygen via a nose cone at a dose of 4% and 2% at a flow rate 0.5 liter/min, respectively. Prior to peptide administration, the colon of each mouse was cleaned with a tap water lavage to remove debris. The conventional white light endoscope was used first with a color camera to identify the presence of adenomas. The colon was then rinsed with water until all of the visible mucous was removed. The Cy5.5-labeled peptides were then delivered at a concentration of 100 μM in 1×PBS containing 2.5% DMSO (phosphate buffered saline) through the instrument channel. The peptides were allowed to incubate for 5 minutes, and then the colon was cleansed 3 times with a tap water to remove any unbound peptide. Prior to imaging, the colon was inspected for residual peptide solution, and when clean, the colon was insufflated with air for imaging. Fluorescence images were collected using Axiovision 4.8.1 software.

Fluorescence Image Analysis

Images collected during endoscopy were recorded as .zvi files and converted into .tiff images using Axiovision Lite software. Consecutive white light and fluorescence images for each adenoma were analyzed. Regions of interest (ROI) around the adenoma and adjacent normal-appearing mucosa were defined on the color and fluorescence images using Labview®. The white light image was utilized to draw an ROI around the adenoma or adjacent normal appearing colonic mucosa which was then superimposed onto the fluorescent image. Mean gray scale values were calculated for each ROI, and an adenoma/normal colon, or a T/B ratio, value was then calculated for each adenoma. The mean fluorescence intensities were calculated from each ROI to determine the ratio of the average intensities for the adenomas to that from adjacent normal-appearing mucosa, or T/B ratio.

Statistics

Two-tailed independent samples t-tests (significance level at α=0.05) were used to determine statistical significance between the T/B ratio for the QPI-Cy5.5 and YTT-Cy5.5 peptides binding to colonic adenomas in the CPC;Apc mice. All statistical computations were processed either using statistical software (SPSS15.0.; SPSS, Chicago, Ill.) or Minitab (Minitab Inc. State College, Pa.).

Summary of Results

In the NIR fluorescence images collected endoscopically in real time (10 Hz) from the colon of CPC;Apc mice in vivo, a white light image showed spontaneous colonic dysplasia on the left side. The NIR reflectance image showed amorphous surface texture from dysplasia, and several bright regions of specular reflection. The corresponding fluorescence image revealed significant contrast enhancement from binding of the QPI-Cy5.5 peptide to dysplasia but not to adjacent normal-appearing colonic mucosa. The margins between dysplasia and normal mucosa were quite sharp in comparison to that on the white light and reflectance images. On an expanded view, heterogeneous, oval structures representing individual crypts could be appreciated, magnification 4×. The corresponding histology (H&E) revealed the features of dysplasia, including elongated nuclei, disorganized crypt structure, hyperchromaticity, and crowed lamina propria, similar to that found in human disease. The fluorescence images from the same region of mucosa with administration of the control peptide YTT-Cy5.5 and with no peptide reveal negligible signal.

This method for performing targeted in vivo optical imaging that integrates a highly-specific peptide with a wide-field NIR fluorescence endoscope achieved a sub-cellular system resolution of <10 µm, representing a significant improvement over previous NIR instruments, and was able to visualize individual dysplastic crypts with well-defined features and sharp lesion borders in real time.

The ability to attain this level of performance in hollow organs of the digestive tract is useful for visualization of drug transport. The fast binding kinetics of the peptide allows for imaging to be performed within only a few minutes after administration, a time interval that is compatible with practical laboratory and clinical use. Topical application provides local disease contrast enhancement without increased background from the probe accumulating within the circulation. Other molecular probe platforms, such as antibodies and activatable probes, have much slower onset and longer clearance, requiring hours (or even days) to reach peak effect, limiting utility and increasing background.

The use of NIR fluorescence has advantages over that of visible for performing in vivo imaging since less background is observed. In addition, the resolution is far better than that of NIR endoscopes that use a fiber-optic bundle, which are limited by pixilation artifact. NIR systems have also been developed for intra-operative imaging, but these instruments are large and not minimally invasive. Furthermore, NIR tomography has been used to image hollow organs, but this approach is limited by light penetration depth and multiple air-tissue interfaces. In addition to the colon, this imaging system can be used to study other hollow organs in small animal models of disease, such as the esophagus and oropharynx. The instrument can be easily adapted to image multiple spectral bands with the addition of appropriate lasers, optics, and filters. Furthermore, this technology can be translated to the clinic to perform high resolution molecular imaging in hollow organs. Some of the unique advantages of this integrated platform can also realized by imaging the deep red region of the visible spectrum and by using other targeting molecules and optical reporters (fluorescent proteins expressed by genetically-engineered mice).

Example 11

Pre-malignant colonic lesions that have non-polypoid (flat and depressed) morphology are indistinguishable on colonoscopy and may confer a high risk for malignancy. A peptide specific for flat dysplasia was identified by phage display technology with HT29 and Hs738.st/int. cells as the positive and negative biopanning substrates, respectively. Bound phage counts, ELISA, flow cytometry, competitive inhibition, binding affinity and fluorescence microscopy were performed to validate specific candidate binding on cultured cells. Confocal and stereomicroscopy was performed on biopsy and endoscopic mucosal resected specimens, respectively, to validate specific peptide binding to dysplastic human colonic mucosa.

Cell Lines and Cultures

The human colorectal adenocarcinoma (HT29) and non-malignant intestinal cells (Hs738.St/Int.) were obtained from the American Type Culture Collection (ATCC, Manassas, Va.). The HT29 cells were cultured in McCoy's medium (Gibco, Calif., USA) containing 10% fetal bovine serum (FBS, Gibco, Calif., USA) and 1% penicillin/streptomycin (Invitrogen Corp. USA). Hs738.St/Int. cells used as controls were cultured in DMEM (Gibco, Calif., USA) containing 10% FBS, 1% penicillin/streptomycin and 1% glutamax. Both cells were cultured at 37° C. in 5% $CO_2$. The cells were passaged using 0.25% EDTA containing trypsin (Mediatech Inc. Mansas, Va.).

Peptide Selection

Peptide selection was performed using phage display technology (Ph.D.-7, New England Biolabs, Beverly, Mass.), and a biopanning strategy based on a subtractive whole-cell approach (20-22). HT29 and Hs738.St/Int. cells were grown to log-phase, detached either with cell dissociation buffer (Invitrogen, Carlsbad, Calif.) or trypsin with 0.25% EDTA (Mediatech Inc. Mansas, Va.), and immersed in blocking buffer, PBS with 1% bovine serum albumin (BSA), for 30 min at 4° C. with continuous agitation. Then 3 rounds for clearing of non-specific binders were performed by incubating ~$10^6$ Hs738.St/Int. cells with a total of ~$10^9$ plaque-forming units (pfu) for 30 min at 4° C. The cleared phages in the supernatant were amplified and titered per manufacturer instructions. The amplified titer ($2\times10^{11}$) was used for further positive selection against HT29 cells (~$10^7$) in PBS containing 0.2% Tween-20 (PBST) for 60 min at 4° C. The cells were washed 3× with cold PBST. The bound phages were then eluted with 1 ml of 0.2 M glycine (pH 2.2) containing 0.1% BSA for 8 min, and immediately neutralized with 150 µl of 1 M Tris buffer (pH 9.2). The eluted phages were amplified, precipitated and titered per manufacturer instructions. The resulting phages ($2\times10^{11}$ pfu) were used to perform 4 additional rounds of biopanning for positive selection against HT29 cells, enriching the pool of candidate phage. After round 3 of in vitro panning, 60 plaques were randomly selected in each round and their sequences were analyzed with an ABI Automatic DNA Analyzer. A primer 5'-CCC TCATAG TTA GCG TAA CG-3' (SEQ ID NO: 28) (−96 gIII sequencing primer, New England Biolabs) corresponding to the pIII gene sequence of the M13 phage was used for sequencing.

After 3 rounds of negative selection with Hs738.St/Int. and 5 rounds of positive selection with the HT29 cells, the pool of candidate phage was enriched by 78 fold [$10\times10^2$/µl ($1^{st}$ round) vs. $78\times10^3$/µl ($5^{th}$ round)]. A total of 60 clones from the $5^{th}$ round yielded the following amino acid sequences in multiplicity: SILPYPY (4) (SEQ ID NO: 9), KCCFPAQ (13) (SEQ ID NO: 2), YRAPWPP (3) (SEQ ID NO: 10), QPWPTSI (3) (SEQ ID NO: 11), WPTPPYA (1) (SEQ ID NO: 12) and MHAPPFY (1) (SEQ ID NO: 13). These sequences were also repeated multiple times in the $3^{rd}$ and $4^{th}$ rounds, further suggesting enrichment. Multiple sequence alignment analysis using RELIC software did not reveal significant homology among these repeated sequences. Only some short motifs such as PP/FP/WP were found.

These sequences were further tested with HT29 and Hs738.St/Int. cells, and bound phages were recovered in triplicate and tittered. Preferential binding of the candidate phage to HT29 cells was validated by bound phage counts. The candidate and non-insert wild-type (WT) phages (M13KE, New England Biolabs) were amplified, precipitated and titered. HT29 and Hs738.St/Int. (~5×10$^6$) cells were grown to log-phase, detached, and blocked, as described above. A total of 2×10$^{11}$ pfu of either the candidate or WT phages were incubated with these cells for 15 min with continuous gentle agitation at room temperature, hereafter RT. After 3 rounds of washing with PBS/0.2% Tween-20, the bound phages were eluted from the cells with 0.2 M glycine (pH 2.2) containing 0.1% BSA buffer for 8 min and tittered. The number of plaques was counted, and the number of candidate phage that bound to the target cells was compared with that found for the control cells as well as that for no-insert WT phage.

The number of KCCFPAQ (SEQ ID NO: 2) phages that bound to the HT29 cells was found to be ~7-fold higher as compared to Hs738.St/Int. (4.3×10$^6$±2.8×10$^5$ versus 6.8×10$^5$±6.0×10$^4$) and 143 times higher when compared to that for non-insert WT phage (3.0×10$^4$±2.5×10$^3$), p-value<0.001. Based on this result, the KCCFPAQ (SEQ ID NO: 2) peptide was selected for further studies. The other sequences did not provide a significant difference in binding between HT29 and Hs738.St/Int. cell and were not used further. This peptide sequence were analyzed with the National Center of Biotechnology Information BLAST (Basic Local Alignment Search Tool). While complete homology for the entire sequence was not found, this peptide has partial homology (KCCF***) to the extracellular domain of ErbB-2 protein which may function as a mimic of a CCY/F motif present in EGF like domain of ErbB family member ligands.

Cell Based ELISA

Preferential binding of the candidate phage to HT29 cells was also validated by cell based ELISA. HT29 and Hs738.St/Int. (2×10$^5$) cells were detached and blocked, as described above, and incubated with 2×10$^{11}$ pfu of either the candidate or WT phages for 20 min at RT in triplicate. After washing 3× with PBS/0.2% Tween-20, the cells were incubated with anti-M13 antibody (IgG) conjugated to horseradish peroxidase (HRP, 1:2000 dil.) (Amersham, Piscataway, N.J.) for 60 min at RT with continuous agitation. After washing 2× with PBST; tetramethylbenzidine (TMB) substrate (Sigma, Saint Louis, Mo.) was added to the cells and developed for 3 min at RT. The reaction was quenched with the 1N H$_2$SO$_4$ and incubated further for 30 min to observe the final end point at RT. The optical density (absorbance) was measured at 450 nm. Cells that were not administered the phages were used as control and subtracted from binding with candidate phages.

On ELISA, the optical density (O.D.) at 450 nm for the KCCFPAQ (SEQ ID NO: 2) phage with HT29 cells compared to that for Hs738.St/Int. cells was 0.67±0.06 versus 0.14±0.03, p<0.002. The ELISA result for the non-insert WT phage with HT29 cells was 0.14±0.04, p<0.002 and 0.06±0.01, p<0.002 for HS738.St/Int. cells Synthesis of Peptides The candidate and control peptides were produced by solid phase synthesis with Fmoc chemistry. Fmoc protected L-amino acids were used, and synthesis was assembled on rink amide MBHA resin using a PS3 (Protein Technologies, Inc. AZ) automatic peptide synthesizer. Isomer I of fluorescein isothiocyanate (5-FITC) was labeled at the C-terminus on the side chain of the lysine residue via a GGGSK linker (SEQ ID NO: 14). The glycine residues provide a spacer function that prevents stearic hindrance between the binding motif and the fluorescent label. Also, the GGGS (amino acids 1-4 of SEQ ID NO: 14) residue provides the same orientation of the peptide relative to the fluorescence label as that for the phage. Moreover, this spacer has the same amino acid sequence as that on the pIII coat protein of the M13 bacteriophage.

The unlabeled peptides were also synthesized for the competitive binding study. Cleavage of the peptides from the resin was achieved by treatment with a mixture of 3 ml TFA:TIS:H$_2$O (95:2.5:2.5 v/v/v) at RT for 4 hr (Sigma Aldrich, St. Louis, Mo.). After filtration and washing of the resin by TFA, a gentle stream of nitrogen was used to remove the excess TFA. The crude peptide was triturated with diethyl ether chilled at −20° C. and then centrifuged at 3,000 rpm for 10 min at 4° C. The crude product was purified by prep-HPLC with a C$_{18}$ column (Waters Inc. Milford, Mass.) using a water (0.1% TFA)-acetonitrile (0.1% TFA) gradient. Successful synthesis was confirmed by Liquid Chromatography/Electro Spray Ionization mass spectrometry (Platform II, micromass, Manchester, UK) and its purity (>95%) was confirmed by reverse phase analytical HPLC (2489 Breeze system, Waters Inc.) using a C$_{18}$ column.

Flow Cytometry Analysis

Preferential binding of the candidate peptide labeled with 5-FITC to the target and control cells was also validated using flow cytometry. HT29 and Hs738.St/Int. (~2×10$^5$) cells were grown, detached, and blocked, as described above. These cells were incubated with the 5-FITC labeled candidate or control peptide (10 μM) for 60 min at 4° C. with continuous agitation. The cells were then washed 3× with cold PBST followed by immediate fixation for 10 min with 4% paraformaldehyde. The cells were washed again with PBS and resuspended in 1 mL of PBS. Flow cytometry was performed using FACSDiVa (BD® LSRII, BD Biosciences, San Jose, Calif.) and analyzed using Flowjo analysis program (Tree Star Inc. Ashland, Oreg.).

On flow cytometry, the KCCFPAQ (SEQ ID NO: 2) peptide bound to 97% of the total HT29 cell population compared to 2.3% for a control peptide. Furthermore, both the candidate and control peptides bound minimally to the Hs738.St/Int. cells. The control peptide (GGGAGGGAGGGK) (SEQ ID NO: 21) was designed with multiple glycines and alanines to have different structure and properties in terms of net charge and side chains from the target peptide. The control peptide is labeled with the same 5'-FITC fluorophore, and has the same number of amino acids as that of the target peptide.

Fluorescence Microscopy

Preferential binding of the FITC-labeled candidate and control peptides to the target and non-target cells was further validated via fluorescence microscopy. HT29 and Hs738.St/Int. cells were grown on cover slips to ~80% confluence. Blocking of non-specific binding was performed by adding PBS/0.5% BSA for 30 min. The cells were then incubated with 10 μM of 5-FITC-labeled candidate or control peptide at either 4 or 37° C. for 15 min followed by staining with 1 μg/mL Hoechst dye (Sigma Aldrich, St. Louis, Mo.) along with the peptide. The cells were washed 3× with PBS and fixed with 4% paraformaldehyde at RT for 10 min. After fixation, the cells were washed again with PBS and mounted with ProLong Gold reagent (Invitrogen, Carlsbad, Calif.) and fluorescence images were collected with confocal microscopy (Leica TCS SP5 Microsystems, Bannockburn, Ill.).

The fluorescent-labeled peptide KCCFPAQ (SEQ ID NO: 2) binds to the surface of the HT29 cells at 4° C. on fluorescence microscopy. Binding of this peptide is confined to the plasma membrane of the HT29 cells, as revealed by the overlay image of the cells stained with 4',6-diamidino-2-phenylindole. No binding is seen to the Hs738.St/Int. cells. The fluorescent-labeled control peptide did not bind to either the HT29 or Hs738.St/Int. cells. The ability of the KCCFPAQ (SEQ ID NO: 2) peptide to internalize at 37° C. is demonstrated by the presence of diffuse peptide staining throughout the cells on the images collected at 15 and 30 min.

Competitive Inhibition Assay

Bound phage counts were performed to observe the competitive inhibition effect of the synthetic candidate heptapeptide with its representative phage counterpart in triplicate. HT29 cells ($5\times10^6$) were detached with enzyme free cell dissociation buffer and blocked with 1% BSA containing PBS for 30 min at 4° C. The cells were washed and incubated with phage ($2\times10^{11}$) for 15 min. Then, the cells were washed with PBS and immediately incubated with different concentrations of unlabeled peptide ranging from 10 to 200 µM for an additional 15 min. Cells were washed 3× and the bound phages were recovered as described above in bound phage counts. The bound phages were then tittered and counted, and the relative inhibition rate was calculated. The inhibition activity of no-insert WT phage by synthetic candidate peptide and phage with unrelated synthetic control peptide were used as negative controls.

The results of the competition assay showed that the unlabeled synthetic KCCFPAQ (SEQ ID NO: 2) peptide in concentrations from 0 to 200 µM reduced binding of KCCFPAQ (SEQ ID NO: 2) phage to HT29 cells in a dose-dependent manner, $4.3\times10^6\pm2.7\times10^5$ to $3.8\times10^4\pm6.6\times10^3$ with $p<0.001$, demonstrating binding inhibition. The rate of inhibition saturated (>98%) when the peptide concentration increased above ~75 µM. No inhibition was observed with addition of up to 200 µM of the control peptide, $p<0.001$. Similarly, addition of the KCCFPAQ (SEQ ID NO: 2) peptide did not inhibit WT phage, $2.6\times10^{14}\pm2.7\times10^3$ versus $2.5\times10^4\pm3.5\times10^3$. These results suggest that binding of the KCCFPAQ (SEQ ID NO: 2) phage to the surface of HT29 cells depends on the specific insert peptide sequence rather than other phage coat proteins.

Measurement of Binding Affinity

The binding affinity of candidate peptide was measured by varying the concentration of the 5-FITC-labeled peptide incubated with the HT29 cells ($1\times10^5$) until saturation of fluorescence intensity was achieved (24). The FITC-labeled peptide was serially diluted in PBS at concentrations that varied from 0 to 70 µM and incubated with the HT29 cells at 4° C. for 1 hr. The unbound peptide was rinsed off the cells by washing 3× with cold PBS/0.2% Tween-20 solution. The cells were resuspended in 200 µL of PBS and transferred to a 96 well plate. Then the fluorescence intensity I was measured at 525 nm using 485 nm excitation on a multi-well plate reader (CytoFluor Series 4000). These results were compared to the fluorescence intensities from the peptide alone (no cells) at concentrations that varied from 0 to 70 µM. These intensities were used to calculate the equilibrium dissociation constant $K_d=1/K_a$ by performing a least squares fit of the data to the non-linear equation $I[X]=(I_0+I_{max}K_a[X])/(I_0+K_a[X])$. $I_0$ and $K_{max}$ are the initial and maximum fluorescence intensities, corresponding to no peptide and at saturation, respectively, and [X] represents the concentration of the bound peptide. Origin 6.1 data analysis software (Origin Lab Corp, Northampton, Mass.) was used to perform a non-linear least square fit of the data.

The relative fluorescence intensity at 525 nm as a function of the concentration of the fluorescent-labeled KCCFPAQ (SEQ ID NO: 2) peptide bound to the HT29 cells was determined. A non-linear increase in fluorescence intensity with peptide concentration was observed until saturation was reached. A fit of the data with the model yields a $K_d=65$ nM/L, $R^2=0.988$.

Peptide Immunohistochemistry

All specimens were obtained with approval from the University of Michigan Institutional Review Board (IRB). Freshly resected specimens of human colonic mucosa were frozen in OCT and sectioned with 10 µm thickness. The sections were then air dried, washed with PBS, and incubated with the FITC-labeled peptides at a concentration of 10 µM for 15 min at RT. The sections were washed 3× for 1 min in PBS and fixed with 4% paraformaldehyde for 10 min. After fixation, the sections were washed again and mounted with ProLong Gold reagent with DAPI (Invitrogen, Carlsbad, Calif.). The sections were imaged under a confocal microscope (Leica TCS SP5 Microsystems, Bannockburn, Ill.). Adjacent sections were sent for routine histology. The intensity for each image was calculated using Matlab (Mathworks, Natick, Mass.).

The FITC-labeled KCCFPAQ (SEQ ID NO: 2) peptide selectively stains dysplasia and adenocarcinoma in comparison to normal colonic mucosa on sections of freshly resected human specimens. The KCCFPAQ (SEQ ID NO: 2) peptide demonstrated no binding to normal colonic mucosa (n=21), but consistently stains dysplasia (n=8) and adenocarcinoma (n=19). The FITC-labeled control (GGG) peptide did not stain any of the specimens, including normal, dysplasia, and adenocarcinoma.

Stereomicroscopic Validation on EMR Specimens

Binding of the candidate or control peptide to the dysplasia on freshly resected human specimens via endoscopic mucosal resection (EMR) was validated on fluorescence stereomicroscopy. Patients with previously diagnosed polypoid and non-polypoid dysplasia who were referred for EMR were recruited. Institutional review board approval was obtained from the VA Palo Alto Health Care System, and informed consent was acquired. After resection, the specimens were rinsed in PBS 3× to remove debris and mucous. An autofluorescence image was acquired before incubating with the peptide. Then, specimens were incubated with either the FITC-labeled candidate or control peptide at a concentration of 10 µmol/L for 5 min. The unbound peptide was rinsed off with PBS 3×. The mucosal surface of the specimen was oriented face up, and a dab of ink was applied to the upper border as a landmark to register the white light and fluorescence images with histology. A white light image was collected from the specimen with and without an overlying transparent grid that contains squares with dimensions of 1×1 mm². Fluorescence images were collected at 500 milliseconds per frame (with the overlying grid removed) using a stereomicroscope (Olympus SZX-16 equipped with Rolera camera; Olympus Corp, Tokyo, Japan) using 477 to 500 nm excitation and 500 to 630 nm emission. A correction to the fluorescence images was performed because the intensity at the center of the image is greater than that in the periphery due to differences in distance. A fluorescence image was collected from a solution of 10 µM FITC in a plate to provide a uniform target for calibration, allowing for quantitative analysis over the entire field of view. After the fluorescence intensities were corrected, lines along the length of the specimen spaced by 2-mm intervals in each image were identified using the grid from the white light image. The mean intensity from each 1×1 mm² interval along this length of tissue was calculated using Matlab and compared with histology. Histopathologic interpretation was performed by a gastrointestinal pathologist (HA) who classified the specimens stained with H&E as normal colonic mucosa, dysplasia, or adenocarcinoma. The histopathologic evaluation of the EMR specimens was conducted at VA Palo Alto Health Care System (AM) and classified as either dysplasia or normal mucosa.

Increased intensity from the FITC-labeled peptide binding can be observed in the region of flat dysplasia as compared to the normal mucosa in the fluorescence image. An expanded view of the histology from the surface epithelium revealed features of dysplasia, notably the flat morphology of the surface epithelium. Using the same instrument settings, there was no visually recognizable autofluorescence from the tissue prior to the peptide incubation, suggesting that the observed fluorescence is due to peptide binding alone.

Quantitative evaluation of the fluorescence intensities on immunohistochemistry showed that the KCCFPAQ (SEQ ID NO: 2) peptide binds 3.1 times greater to adenocarcinoma (31.5±6.0 AU) compared to normal mucosa (10.1±3.6 AU), p<0.001 and 1.5 fold higher than dysplasia (21.1±3.8 AU), p<0.001. The target-to-background (T/B) ratio for the KCCFPAQ (SEQ ID NO: 2) peptide vs. control peptide was 3.6, 3.1, and 2.0 for adenocarcinoma, dysplasia and normal mucosa, respectively on frozen sections.

The fluorescence intensities (mean±SEM) for the 3 histologic classifications from the EMR specimens associated with binding by the KCCFPAQ (SEQ ID NO: 2) and control peptides on stereomicroscopy were determined. For the candidate peptide, the results for normal mucosa (n=15), polypoid dysplasia (n=24) and non-polypoid dysplasia (n=16) were 43.5±10.7, 78.6±12.8 and 85.1±19.2 AU, respectively, p<0.001. For the control peptide, the intensities for normal mucosa (n=6), polypoid dysplasia (n=5) and non-polypoid dysplasia (n=2) were 16.5±2.5, 14.0±3.0 and 21.8±4.1 AU, respectively. The T/B of KCCFPAQ (SEQ ID NO: 2) peptide for flat adenoma to adjacent normal mucosa was found to be higher by ~2.0 fold whereas T/B for polypoid adenoma to adjacent normal mucosa was 1.8.

Statistical Analysis

To evaluate competitive binding between the candidate phage and peptide, the differences in mean phage counts were first compared using a one-way analysis of variance (ANOVA), and differences in the mean value between classifications were evaluated using Tukey's multiple comparisons of the means ($\alpha=0.05$). Similarly, differences in the mean intensity for all histopathological classifications were evaluated as described above. Statistical significance was assessed at the 0.01 level. For all other validation experiments, a comparison of the difference in the mean findings between 2 groups was performed using a 2-sided independent samples t-test ($\alpha=0.05$). All data are presented as mean±SD unless otherwise specified. A p-value<0.05 was considered to be significant.

Summary of Results

The 7mer sequence KCCFPAQ (SEQ ID NO: 2) was selected after 5 rounds of enrichment, and specific binding of this peptide to HT29 cells was observed in culture. A dose-dependent reduction in binding was observed on competition with unlabeled peptide, an affinity of $K_d=65$ nmol/L was measured, and specific binding to the plasma membrane of HT29 cells was observed on fluorescence microscopy. On biopsy specimens (n=28), the fluorescence intensity (mean±SEM) from sections classified histologically as normal mucosa (n=21), dysplasia (n=8), and adenocarcinoma (n=19), was 10.1±3.6, 21.1±3.8, and 31.5±6.0 AU, respectively, p<0.001. Similarly, a significant difference in fluorescence intensity was observed among normal mucosa (n=15, 43.5±10.7), polypoid dysplasia (n=24, 78.6±12.8) and non-polypoid dysplasia (n=16, 85.1±19.2) on human EMR specimens, p<0.001.

The peptide sequence KCCFPAQ (SEQ ID NO: 2) binds specifically to pre-malignant human colonic mucosa with non-polypoid morphology and can be fluorescent-labeled to target these lesions on endoscopic imaging in patients. This peptide can therefore be used as a targeted contrast agent for enhancing diagnostic specificity on endoscopy. These validated results support its use with novel imaging instruments, including fluorescence endoscopes and confocal endomicroscopes that are being used in the clinic. Fluorescent-labeled peptides such as KCCFPAQ (SEQ ID NO: 2) are thus contemplated for use, for example, in targeting pre-malignant and malignant lesions during colonoscopy for guiding tissue biopsy, identifying flat and depressed lesions, and localizing tumor margins in patients at increased risk for developing adenocarcinoma. Such fluorescent-labeled peptides can also be used to visualize flat and depressed lesions that occur in the setting of ulcerative colitis, as molecular targets associated with cancer progression are frequently preserved in different disease processes.

Example 12

Gastrointestinal cancers are heterogeneous and can over-express several gene targets that can be imaged simultaneously on endoscopy using multiple molecular probes. A multi-spectral scanning fiber endoscope was developed for wide-field fluorescence detection of colonic dysplasia. Excitation at 440, 532 and 635 nm was delivered into a single spiral scanning fiber, and fluorescence was collected by a ring of light-collecting optical fibers placed around the instrument periphery. Specific-binding peptides were selected with phage display technology using the CPC;Apc mouse model of spontaneous colonic dysplasia. Validation of peptide specificity was performed on flow cytometry and in vivo endoscopy. The peptides KCCFPAQ (SEQ ID NO: 2), AKPGYLS (SEQ ID NO: 25), and LTTHYKL (SEQ ID NO: 26) were selected and labeled with 7-Diethylaminocoumarin-3-carboxylic acid (DEAC), 5-Carboxytetramethylrhodamine (TAMRA), and CF633, respectively. Separate droplets of KCCFPAQ-DEAC, AKPGYLS-TAMRA, and LTTHYKL-CF633 were distinguished at concentrations of 100 and 1 µM. Separate application of the fluorescent-labeled peptides demonstrated specific binding to colonic adenomas.

Multi-Spectral Scanning Fiber Endoscope

A scanning fiber endoscope system was adapted for fluorescence detection in three channels (RGB) using excitation at 440 (NDHB510APA, Nichia, Tokyo, Japan), 532 (FTEC532-V10TA0, Blue Sky Research, Milpitas, Calif.) and 635 (FMXL635-017TA0B, Blue Sky Research) nm using an RGB coupler (OZ Optics, Ottawa, Canada). The three laser sources are delivered simultaneously into the scanning fiber, and focused to the same point on the illumination plane using a custom lens assembly, as shown in the schematic in FIG. 2A. The laser power coming out of the distal tip of the endoscope is <2 mW for each channel, a level consistent with a non-significant risk (NSR) determination by the U.S. Food and Drug Administration (FDA, 21 CFR 812) for future human clinical studies. The amplitude of the spiral scanner was reduced to achieve a divergence angle of 70 deg (max 100 deg) to minimize noise in the periphery of the image. Fluorescence is collected by a ring of 12 step-index plastic optical fibers (POF) with numerical aperture (N.A.) of 0.63 and outer diameter of 250 µm (Toray Industries Inc, Tokyo, Japan).

The detection system, shown in FIG. 2B, uses longpass ($\lambda_{LP}=450$ nm) and notch ($\lambda_{N1}=532$ nm and $\lambda_{N2}=632.8$ nm) filters (Edmund Optics Inc, Barrington, N.J.) to reject the reflectance component (RGB laser excitation) of the light emerging from the collection fibers. The fluorescence component is deflected into three individual channels using dichroic beamsplitters DM1 ($\lambda_c=460$ nm) and DM2 ($\lambda_c=550$ nm) (Chroma Technology Corp, Bellows Falls, Vt.). An additive RGB set of dichroics ($\lambda_{R,G,B}$, part#52-546, Edmund Optics Inc) is used to filter the individual fluorescence beams, which are focused onto separate PMT (H7826-01, Hamamatsu Corp, Hamamatsu City, Japan) detectors using an objective lens ($O_{R,G,B}$, f=25 mm, N.A.=0.46). The PMT signals are sampled at 25 MHz to generate video rate (30 Hz) images.

The distal tip of the flexible multi-spectral endoscope had a 1.6 mm outer diameter). The distal end of the single illumination optical fiber was scanned in 250 circles in a growing spiral pattern at approximately 11.5 kHz. Real-time zooming to the diffraction limit of the optics can be performed by reducing the scan angle while capturing the same number of pixels over the FOV. The sub-millimeter lens assembly seals the distal tip of the instrument and extends the waist of the laser beam to define a depth of focus that ranges between 2 to 50 mm. A spatial resolution of <15 µm was achieved at a distance of 3 mm from the distal tip to the illumination plane and <1 mm at the maximum depth of focus. This unique combination of scanning mechanism and optics allows for a flexible instrument to be realized in a much smaller package yet match the high-quality images from standard medical endoscopes.

Peptide Selection and Validation

Cell culture reagents were purchased from Invitrogen (Carlsbad, Calif.). Chemical reagents were purchased from Sigma-Aldrich (St. Louis, Mo.) unless otherwise noted. Mice were cared for under the approval of the University Committee on the Use and Care of Animals (UCUCA) at the University of Michigan. Five- to seven-month old CPC;Apc mice that have a Cre-regulated somatic mutation in one Apc allele, causing adenomas to develop spontaneously in the distal colon at approximately 3 months of age, were used. This mutation is commonly found in sporadic human colorectal cancer. All mice were housed in specific pathogen-free conditions and supplied water ad libitum throughout the study. Peptide selection was performed with in vivo phage display technology using this mouse as the biopanning substrate.

A 7-month old CPC;Apc mouse was injected via tail vein with $2 \times 10^{11}$ pfu of the parent M13-7mer Ph.D.7™ Phage Display Library (New England Biolabs, Beverly, Mass.). The library was allowed to circulate for 10 min, after which the mouse was euthanized by carbon dioxide asphyxiation and immediately heart-perfused with phosphate buffer solution with protease inhibitors (PBS-PI): 1 mM phenylmethanesulfonylfluoride (PMSF), 20 µg/mL aprotinin, and 1 µg/mL leupeptin). Organs were extracted after perfusion and kept on ice. The bound phages were recovered by homogenizing each tissue or organ (Bio-gen Pro 200) in DMEM-PI (Dulbecco's Modified Eagle Medium plus protease inhibitors: 1 mM phenylmethanesulfonylfluoride (PMSF), 20 µg/mL aprotinin, and 1 µg/mL leupeptin). The tissue samples were washed 3× with ice-cold washing medium (DMEM-PI containing 1% bovine serum albumin (BSA)), centrifuging for 5 min at 3000 rpm between each wash. After the last wash, freshly starved *Escherichia coli* (ER2738) were added to each tissue homogenate and incubated for 30 min at room temperature (RT). Pre-warmed Luria-Bertani (LB) medium was then added to the bacteria-homogenate solution and incubated for an additional 30 min at RT. The supernatant was recovered after centrifugation and tittered to determine the number of bound phage within each tissue tested. This procedure constituted one round of biopanning. A total of 3 rounds of phage biopanning were performed, with amplification of the recovered eluate after each biopanning round. The input phage number ($2 \times 10^{11}$ pfu) was kept constant for each round of biopanning. Tittering was performed with appropriate serial dilutions for both eluted phage and amplified phage after each round of biopanning. Agar plates treated with IPTG (isopropyl-b-D-thiogalactosidase) and Xgal (5-bromo-4-chloro-3-indoyl-b-D-thiogalactosidase) were able to visually identify plaques using blue/white screening. Amplified phages from selected phage plaques were purified by PEG/NaCl (polyethylene glycol/sodium chloride) precipitation. All M13 DNA were sequenced after isolating single stranded DNA using an iodide buffer extraction via dideoxy chain termination using a DNA sequencer (Applied Biosystems, 3730XL DNA Analyzer, UM DNA Core) with the NEB-96 gIII sequencing primer provided by New England Biolabs (# S1259S). The number of phages bound to each organ or tissue was calculated as the output pfu/(input pfu×tissue mass).

Specific binding of the candidate peptides to primary dysplastic colonic epithelial cells were validated on flow cytometry ex vivo and with small animal endoscopy in vivo using FITC-labeled peptides using a non-scanning white light endoscope.

After three rounds of in vivo phage biopanning that included heart perfusion as a method for clearing non-specific vascular binders, the preference of the phage pools collected during all rounds of biopanning indicated that the phages were binding more specifically to colonic adenomas in comparison to normal appearing adjacent colonic mucosa, kidney and liver. Phages that bound to colonic adenomas approximately 10 times greater in number than to normal appearing colonic mucosa were chosen. As a result, 42 individual phage clones were sequenced from the third round of biopanning, and were individually amplified and conjugated to 5'-FITC. Binding to isolated colonic epithelial cells from adenomas for each phage clone was analyzed using flow cytometry. A common 7-mer phage that expresses the sequence HAIYPRH (SEQ ID NO: 29) is a known contaminant, and was run (labeled # in Supplementary FIG. 1B) to ensure the validity of the assay. The T/B ratio for clone HAIYPRH was found to be 1.10±0.08, indicating minimal binding from a non-specific clone, as expected. Six phage clones with a T/B ratio (target to wild-type phage)>1.9 were identified as ALTPTPP (SEQ ID NO: 30), NLVNLLP (SEQ ID NO: 31), ANYPREP (SEQ ID NO: 32), ATTVPAS (SEQ ID NO: 33), LTTHYKL (SEQ ID NO: 26), and AKPGYLS (SEQ ID NO: 25). The KCCFPAQ (SEQ ID NO: 2) peptide had been previously found to bind to human HT29 cells.

The 7 peptides were synthesized and conjugated to 5'-FITC for evaluation of in vivo binding. The GGGAGGG (SEQ ID NO: 34) peptide used as a control. The target and control peptides were prepared using solid phase synthesis with standard Fmoc chemistry. Fmoc protected L-amino acids were used, and synthesis was assembled on rink amide MBHA resin using a PS3 (Protein Technologies, Inc. AZ) automatic peptide synthesizer. The candidate peptides for the validation study were labeled with 5'-FITC (Anaspec, Fremont, Calif.) at the C-terminus on the side chain of a lysine residue via a GGGSK linker (SEQ ID NO: 14). The candidate peptides for the multi-spectral study were labeled with three different organic fluorophores. 7-Diethylaminocoumarin-3-carboxylic acid (DEAC, Sigma-Aldrich, St. Louis, Mo.) has a peak absorption and emission at 432 and 472 nm, respectively. 5-Carboxytetramethylrhodamine (TAMRA, Chempep, Wellington, Fla.) has a peak absorption and emission at 541 and 568 nm, respectively. CF633 (Biotium Inc., Hayward, Calif.) has a peak absorption and emission at 630 and 650 nm, respectively. These dyes have peak absorption that approximately match the laser sources. In addition, the peptide GGGAGGGAGGGK (SEQ ID NO: 21) was used as a control.

In vivo imaging of the 8 FITC-labeled peptides with the non-scanning endoscope demonstrated that KCCFPAQ (SEQ ID NO: 2), AKPGYLS (SEQ ID NO: 25), and LTTHYKL (SEQ ID NO: 26) exhibited the highest T/B ratio for binding to colonic adenomas in vivo, shown in Table 1.

TABLE 1

Summary of imaging results. The average T/B ratios for in vivo imaging of colonic adenomas in CPC; Apc mice are shown for candidate peptides labeled with FITC for validation of specific binding using a non-scanning endoscope and for target peptides labeled with DEAC and TAMRA using the multi-spectral scanning fiber endoscope.

| Peptide | n (Mice) | n (Adenomas) | Average T/B |
|---|---|---|---|
| Non-scanning Endoscopy Results | | | |
| KCCFPAQ-FITC | 3 | 9 | 1.69 ± 0.70 |
| AKPGYLS-FITC | 4 | 7 | 1.53 ± 0.48 |
| LTTHYKL-FITC | 5 | 13 | 1.50 ± 0.73 |
| ALTPTPP-FITC | 3 | 10 | 1.19 ± 0.18 |
| ATTVPAS-FITC | 2 | 3 | 1.06 ± 0.33 |
| NLVNLLP-FITC | 1 | 2 | 0.99 ± 0.06 |
| ANYPREP-FITC | 1 | 2 | 0.94 ± 0.11 |
| GGGAGGG-FITC | 3 | 13 | 1.05 ± 0.05 |
| Multi-Spectral Scanning Fiber Endoscopy Results | | | |
| KCCFPAQ-DEAC | 3 | 7 | 1.71 ± 0.19 |
| AKPGYLS-TAMRA | 3 | 6 | 1.67 ± 0.12 |
| GGGAGGG-DEAC | 2 | 4 | 1.19 ± 0.09 |
| GGGAGGG-TAMRA | 2 | 4 | 1.32 ± 0.10 |

The three peptides were subsequently conjugated to 7-Diethylaminocoumarin-3-carboxylic acid (DEAC), 5-Carboxytetramethylrhodamine (TAMRA), and CF633, respectively, for in vivo imaging with the multi-spectral scanning fiber endoscope. The control peptides GGGAGGGAGGGK (DEAC)-NH$_2$ and GGGAGGGAGGGK (5-TAMRA)-NH$_2$ were also synthesized.

Fluorescence Spectra from Multiple Peptides

A fiber-coupled spectrophotometer (Ocean Optics, Dundin, Fla.) was used to validate the excitation and emission spectra of the fluorescent-labeled peptides. Droplets of each fluorescent-labeled peptide at 1 µM concentration were analyzed individually. The optical collection fibers of the multi-spectral scanning fiber endoscope were disconnected from the base station and connected to the spectrophotometer. Directed data collection was performed by stopping the motion of the scanning fiber and aiming the illumination spot at the droplet. Readings were then acquired using a 3 ms integration time with Ocean Optics Spectra Suite software.

The excitation and emission spectra of the 3 RGB laser sources and fluorescent-labeled peptides over the visible spectrum were measured with the fiber coupled spectrophotometer. The spectra were collected from the labeled peptides both with and without use of the respective dichroic (bandpass) filters a ($\lambda_{R,G,B}$). Excitation at 440 nm and peak emission at 486 nm were observed for the KCCFPAQ-DEAC peptide. Excitation at 532 nm and peak emission at 577 nm were observed for the AKPGYLS-TAMRA peptide. Excitation at 635 nm and peak emission at 659 nm were observed for the LTTHYKL-CF633 peptide. These spectra showed minimal overlap (crosstalk) among the fluorescence emission bands for the 3 peptides. Moreover, these results showed that labeling the peptide with an organic dye causes only a small shift (9 to 14 nm) in the peak emission wavelength.

Individually and Combined Targeted In Vivo Images

The CPC;Apc mice were first imaged with white light using a non-scanning endoscope (Karl Storz Veterinary Endoscopy, Goleta, Calif.) to assess for the presence of colonic adenomas that have a size between ~0.5 to 4 mm in diameter. Any adenomas were rinsed of debris including stool and mucous, by delivering tap water through a 3 Fr instrument channel. Then, the fluorescent-labeled peptides were delivered topically at a concentration of 100 µM in 1×PBS in a volume of 1 mL to the distal 4 cm of the colon and rectum. The peptides were incubated for 5 minutes and then the unbound peptides were rinsed away with tap water 3 times. The colon was inspected for any residual peptide, and when clean, the colon was insufflated with air and imaged with the multi-spectral scanning fiber endoscope. Cre-recombinase negative littermates that do not express colonic adenomas were used as controls.

Videos collected during endoscopy were exported as avi video files and converted into sequential png images using Apple QuickTime. White light and fluorescence images for each adenoma were analyzed in NIH Image J. The white light image was utilized to draw a region of interest (ROI) around the adenoma or adjacent normal appearing colonic mucosa which was then superimposed onto the fluorescence image. The mean fluorescence intensities were calculated for each ROI, and a target/background (T/B) ratio was calculated for each colonic adenoma and compared to the surrounding normal appearing mucosa.

Images were collected with the fluorescent-labeled peptides A) KCCFPAQ-DEAC, B) AKPGYLS-TAMRA, and C) LTTHYKL-CF633 administrated. Specific binding of each peptide to colonic dysplasia is demonstrated by comparing the fluorescence images with the corresponding white light images collected with the non-scanning. The lesion margins on fluorescence appeared to be sharp in comparison to that on the white light images. The fluorescent-labeled peptides KCCFPAQ-DEAC and AKPGYLS-TAMRA clearly displayed specific binding to colonic dysplasia while that for the LTTHYKL-CF633 peptide appears to be more subtle. The average T/B ratios of peptide binding to dysplasia versus normal appearing adjacent colonic mucosa were 1.71±0.19 (range 1.50-2.06) and 1.67±0.12 (1.50-1.78) for KCCFPAQ-DEAC and AKPGYLS-TAMRA, respectively (Table 1), while that for LTTHYKL-CF633 was not measured because of low signal level. Representative histology (H&E) of the adenoma and adjacent normal appearing mucosa showed dysplastic crypts with features, such as enlarged nuclei, disorganization, hyperchromaticity, crowded lamina propria, and distorted architecture, similar to that seen in human sporadic adenomas.

Administration of KCCFPAQ-DEAC and AKPGYLS-TAMRA to normal colonic mucosa resulted in minimal signal, a result comparable to that found with no administration of peptide (autofluorescence). Also, minimal signal is seen for binding of the control peptides GGGAGGG-DEAC and GGGAGGG-TAMRA to the adenomas (arrows), resulting in T/B ratios of 1.19±0.09 and 1.32±0.10 (Table 1), respectively. Statistical differences between the target and control peptides for KCCFPAQ and AKPGYLS were p=0.009 and p=0.001, respectively. A quantitative comparison of fluorescence intensities for binding of the control peptide to adenomas and autofluorescence (no peptide) could not be made because the effect on the low signal levels by the system autogain function.

White light images of colonic adenomas from 3 different mice were examined. Sequential administration of the KCCFPAQ-DEAC and AKPGYLS-TAMRA peptides resulted in separate spatial patterns of binding to colonic dysplasia in the blue and green channels. This result suggests that each peptide binds to a different cell surface target. Combined delivery of the control peptides GGGAGGG-DEAC and GGGAGGG-TAMRA resulted in similar intensity to that found for autofluorescence where no peptide was administered.

Statistical Analysis

All results are shown as mean±one standard deviation. After data normality was established using the Shapiro-Wilk test, two-sided independent samples t-tests were performed to determine statistical significance (significance level defined as $\alpha=0.05$) between the target and control peptides for specific binding to colonic adenomas (PASW Statistics 18, Chicago, Ill.).

Summary of Results

The average target/background ratios were 1.71±0.19 and 1.67±0.12 for KCCFPAQ-DEAC and AKPGYLS-TAMRA, respectively. Administration of these two peptides together resulted in distinct binding patterns in the blue and green channels. Specific binding of two or more peptides can be distinguished in vivo using the multi-spectral endoscope described herein to localize colonic dysplasia on real-time wide-field imaging. The ultrathin dimensions and flexibility of this multi-spectral endoscope allow for seamless integration with standard instrument channels of conventional medical endoscopes. Moreover, the lasers, detectors and data acquisition system are conveniently contained within a portable cart that can be easily transported around a procedure room.

Example 13

A near-infrared (NIR) labeled multimer peptide was generated using trilysine as a dendritic wedge and peptide AKPGYLS (SEQ ID NO: 25). The multimer peptide was labeled with either Cy5.5 or FITC using solid phase synthesis and a real-time near-infrared endoscope was used to visualize the dysplastic lesions in vivo in CPC;Apc mice as follows.

Chemicals and Materials

Human colorectal adenocarcinoma (HT29, SW480) and non-malignant intestinal (CCD841Con) cells were obtained from the American Type Culture Collection (ATCC, Manassas, Va.). The HT29, SW480, and CCD841Con cells were cultured in McCoy's Medium, Dulbecco's Modified Eagle Medium, Eagle's Minimal Essential Medium, and Roswell Park Memorial Institute medium, respectively. All cells were cultured at 37° C. in 5% $CO_2$, and supplemented with 10% fetal bovine serum (FBS), 1% penicillin/streptomycin, and 1% glutamax. The cells were passaged using 0.25% EDTA containing trypsin (Mediatech Inc, Mansas, Va.). The cell number was determined using a hemocytometer. Peptide synthesis reagents were obtained from Anaspec (Anaspec, Fremont, Calif.) or AAPPTEC (AAPPTEC, Louisville, Ky.) and were of the highest grade available (>99% purity) and used without further purification. Solvents and other chemical reagents were purchased from Sigma Aldrich (St. Louis, Mo.) unless otherwise mentioned.

Animals

Mice were cared for under the approval of the University Committee on the Use and Care of Animals, University of Michigan (UCUCA). All mice were housed in specific pathogen-free conditions and supplied water ad libitum under controlled conditions of humidity (50±10%), light (12/12 hr light/dark cycle) and temperature (25° C.) throughout the study.

Peptide Synthesis

Figure 3:
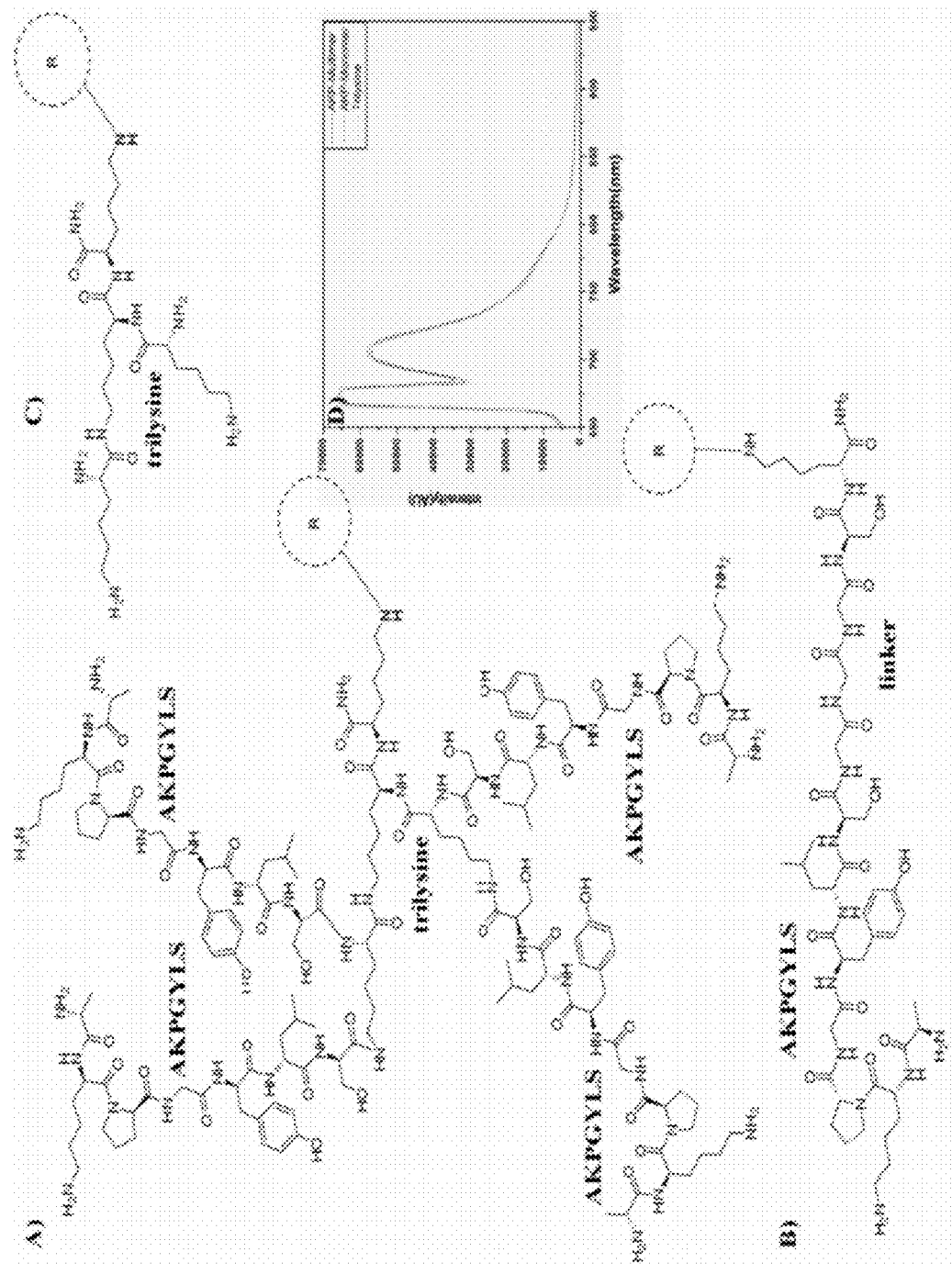
FIG. 3—Chemical structures of molecular probes. A) AKP-multimer, B) AKP-monomer, and C) trilysine core, R indicates either Cy5.5 or FITC label. Different components include peptide binding motif, linker, and fluorescent dye. D) Fluorescence emission spectra of molecular probes labeled with Cy5.5 using $\lambda_{ex}$=671 nm excitation.

The peptides used in this study were prepared using standard Fmoc-mediated solid-phase peptide synthesis on Rink amide MBHA resin. Fmoc and Boc protected L-amino acids were used and synthesis was assembled on rink amide MBHA resin. The peptides synthesized were: 1) AKPGYLSGGGSK-$CONH_2$ (AKP-monomer), 2) tetrameric version of AKPGYLS anchored on a trilysine core (AKP-multimer), and 3) trilysine core alone (control). See, FIG. 3. Peptides were conjugated with either FITC or Cy5.5 for use on flow cytometry or NIR imaging, respectively. For the in vitro studies, FITC was selected because of ease for chemical incorporation and high quantum yield for quantitative assays. For in vivo imaging, Cy5.5 was selected because of lower autofluorescence background, reduced tissue scattering, and resistance to photobleaching.

The monomer peptide was synthesized on a PS3 automatic synthesizer (Protein Technologies Inc., Tucson, Ariz.). The C-terminal lysine was incorporated as Fmoc-Lys (ivDde)-OH and the N-terminal Ala was incorporated as Boc-Ala-OH to avoid unwanted Fmoc removal during deprotection of the ivDde moiety prior to dye labeling. Upon complete assembly of the peptide, the resin was transferred to a reaction vessel for manual labeling with dye. The ivDde side chain protecting group was removed with 5% hydrazine in DMF (3×10 min) with continuous shaking at room temperature (RT). The resin was washed with Dimethylformamide (DMF) and dichloromethane (DCM) 3 times each for 1 min. The protected resin-bound peptide was incubated overnight either with 5-FITC (Anaspec, Fremont, Calif.) or Cy5.5-NHS ester (Lumiprobe LLC, Hallandale Beach, Fla.) with DIEA and the completion of the reaction was monitored by a qualitative Ninhydrin test. Upon completion of labeling, the peptide was cleaved from the resin using TFA:TIS:H2O (95:2.5:2.5 v/v/v; Sigma Aldrich, St. Louis, Mo.) for 4 hours with shaking in the dark at RT. After separation of the peptide from the resin, the filtrate was removed with $N_2$ gas followed by precipitation with diethyl ether and stored overnight at −20° C. The precipitate was centrifuged at 3000 rpm for 5 min and washed with diethyl ether 3 times and centrifuged in between each washing step.

Similarly, the AKP-multimer was synthesized manually on a trilysine-core which has 4-reactive sites for peptide coupling. First, the C-terminus Fmoc-Lys-(ivDde)-OH was conjugated on the resin for specific labeling of the dye followed by deprotection of Fmoc group with 20% piperidine. Next, two consecutive coupling steps were performed with Fmoc-Lys (Fmoc)-OH. After the coupling of second Fmoc-Lys (Fmoc)-OH, the deprotection of Fmoc-group provided the 4-arms for assembling the peptide sequences in a tetrameric form. Then, stepwise solid phase synthesis was performed. As mentioned earlier in monomer synthesis, the Boc-Ala-OH was used at the N-terminus. All other steps after complete assembly were repeated similarly as for monomer peptide synthesis.

The crude peptides were dissolved in 1:1 Acetonitrile/H2O (v/v) and purified by prep-HPLC with a $C_{18}$ column (Waters Inc, Milford, Mass.) using a water (0.1% TFA)-acetonitrile (0.1% TFA) gradient. The final purity of the peptides was confirmed by analytical $C_{18}$-column. Further characterization was performed with either ESI (Waters Inc, Milford, Mass.) or Q-TOF (Agilent Technologies, Santa Clara, Calif.)

mass spectrometry. The chromatogram obtained from analytical RP-HPLC indicated a purity >95% for all peptides. On mass spectra, the experimental m/z (mass units) measured for the AKP-monomer-FITC, AKP-multimer-FITC, trilysine-FITC, AKP-monomer-Cy5.5, AKP-multimer-Cy5.5, and trilysine-Cy5.5 was 1510.0, 3786.0, 919.5, 1727.97, 4003.3, and 1136.7, respectively. These values agree with the expected molecular mass of 1509.8, 3785.9, 919.8, 1726.97, 4002.3, and 1136.7, respectively.

In Vivo Imaging

The binding activity of the synthetic peptides to colonic dysplasia was assessed in vivo in 3 cohorts of CPC;Apc mice: 1) AKP-multimer, n=14 mice with n=33 adenomas, 2) AKP-monomer, n=14 mice with n=27 adenomas, and 3) trilysine core, n=8 mice with n=17 adenomas as a control. For the imaging studies, anesthesia was induced and maintained in the animals with inhaled isoflurane mixed with oxygen via a nose cone at a dose of 4% and 2% at a flow rate of 0.5 liter/min, respectively. Prior to applying the peptides, the colon was prepped using a tap water lavage. The adenomas were viewed endoscopically, and videos were recorded using white light with a small animal endoscope (Karl Storz Veterinary Endoscopy, Goleta, Calif.). The colon was rinsed with water until all mucous and other debris was removed. Adenomas from approximately 0.5-4 mm in diameter that were not covered in debris, including stool and mucous, were included in the study.

The Cy5.5-labeled peptides were delivered at a concentration of 100 μM in PBS containing 2.5% DMSO (dimethyl sulfoxide) through the instrument channel of the endoscope. During peptide administration, 1.5 mL of peptide was delivered to the distal colon in each mouse. The peptide was allowed to incubate for 5 min after which the colon was cleansed 3× with a tap water to remove the unbound peptide. Prior to imaging, the colon was inspected for residual peptide solution, and when clean, the colon was insufflated with air and imaged with the wide field endoscope which provides excitation at 671 nm. Fluorescence and reflectance videos were collected using Axiovision 4.8.1 software. Fluorescence videos were collected at 100 ms/frame (10 Hz), and transferred to the computer for storage by a firewire connection. A filter wheel was incorporated into the handle of the housing to quickly switch between collection of reflectance and fluorescence images. White light, fluorescence and reflectance images were collected from 1) n=14 mice having n=33 adenomas with AKP-multimer, 2) n=14 mice having n=27 adenomas with AKP-monomer, and 3) n=8 mice having n=17 adenomas with the trilysine (control). The CPC;Apc mice imaged ranged in age from 3 to 6 months. Fluorescence images were exported as videos in zvi format (16 bit digital resolution) using LabView software. Sequentially-collected white light and fluorescence images for each adenoma were analyzed. Separate regions of interest (ROI) were defined around the adenoma and adjacent normal-appearing mucosa on the white light image, and the ROI's were overlayed onto the fluorescence images. The target to-background (T/B) ratio was determined by ratioing the mean intensities from these 2 ROI's.

White light endoscopy was performed in to identify adenomas that range in diameter from ~0.5 to 4 mm. No background (autofluorescence) was noticeable using NIR excitation at $\lambda_{ex}$=671 nm from colonic mucosa prior to peptide administration. The reflectance image showed amorphous surface texture from dysplasia with little difference in intensity between normal colonic mucosa and adenoma. Several bright regions of specular reflection were appreciated. The AKP-monomer provided a faint fluorescence intensity that was significantly amplified by the AKP-multimer. The trilysine core (control) showed negligible signal. The use of the AKP-multimer detected all lesions regardless of size whereas AKP-monomer did not visualize lesions smaller than ~1 mm.

A quantitative analysis of image intensities using neighboring regions-of-interest (ROI) revealed that the AKP-multimer produces ~1.8-fold greater average fluorescence intensity from colonic adenomas in comparison to that from the AKP-monomer and the trilysine control with T/B ratios of 3.84±0.26, 2.21±0.13, and 1.56±0.12, respectively, p<0.001. A non-parametric Mann-Whitney analysis showed that AKP-multimer peptide binds in significantly greater amounts to the adenomas than AKP-monomer.

Flow Cytometry

Peptides labeled with 5-FITC were used for the validation assays of cell binding. Preferential binding of the multimer peptide, monomer peptide, and trilysine to different human colorectal cancer (SW480, and HT29) and control cells (CCD841-Con) was validated on flow cytometry. A total of $5 \times 10^5$ cells were used with each probe. The confluent cells were detached using enzyme free cell dissociation buffer (Invitrogen, Carlsbad, Calif.) or trypsin with 0.25% EDTA (Mediatech Inc, Manassa, Va.) and immersed in blocking buffer, PBS with 1% bovine serum albumin (BSA), for 30 min at 4° C. with continuous agitation. After blocking, cells were washed with 1×PBS and spun down for 5 min at 1000 rpm. Then cells were incubated with the 5-FITC labeled peptides and trilysine (10 μM) for 60 min at 4° C. with continuous agitation. The cells were then washed 3× with cold PBST followed by immediate fixation for 10 min with 4% paraformaldehyde. The cells were washed again (1×) with PBS and resuspended in 1 mL of PBS. Flow cytometry was performed using FACSDiVa (BD® LSRII, BD Biosciences, San Jose, Calif.) and analyzed using Flowjo analysis program (Tree Star Inc, Ashland, Oreg.). The gain was kept constant for all experiments.

The AKP-multimer peptide bound specifically to the plasma membrane of the SW480 and HT29 cells but not to CCD-841Con cells, as shown by an overlay of the FITC and DAPI images. The same concentration of AKP-monomer peptide revealed a lower fluorescence intensity at the cell surface. The trilysine core (control) did not stain any of the cells.

Fluorescence Microscopy

Preferential binding of the FITC-labeled peptides to the target and non-target cells as mentioned above was further validated via fluorescence microscopy. Cells (~$7.5 \times 10^3$) were seeded on cover slips to ~80% confluence. The cells were then incubated with 10 μM of 5-FITC-labeled peptides and trilysine at 4° C. for 1 hr followed by staining with 1 μg/mL Hoechst dye (Sigma Aldrich, St. Louis, Mo.). The cells were washed 3× with PBS and fixed with 4% paraformaldehyde at RT for 10 min. After fixation, the cells were washed again with PBS (1×) and mounted with ProLong Gold reagent (Invitrogen, Carlsbad, Calif.) and fluorescence images were collected with confocal microscopy (Leica TCS SP5 Microsystems, Bannockburn, Ill.). The specific peptide binding activity of the FITC-labeled AKP-multimer and AKP-monomer peptides was compared.

The counts reflecting the AKP-multimer binding to SW480, HT29, and CCD-841Con cells were significantly higher by a factor of 20.2, 26.1, and 2.2 times, respectively, than that for unstained cells. As expected, AKP-monomer bound to a lower extent than the AKP-multimer, whereas trilysine (control) bound minimally as compared to cells unstained with peptide. In both experiments, the AKP-multimer peptide bound consistently with the primary human colon adenocarcinoma cell lines. Both cell-binding assays demonstrated that AKP-multimer had higher binding avidity than monomer, which can be attributed to the multivalency effect.

Measurement of Binding Affinity

The binding affinity of multimer and monomer peptide was measured by varying the concentration of the 5-FITC-labeled peptides and trilysine incubated with the target cells ($1\times10^5$) until saturation of fluorscence intensity was achieved [16]. The FITC-labeled peptide was serially diluted in PBS at concentrations that varied from 0 to 10 µM and incubated with the target cells at 4° C. for 1 hr. The unbound peptide was rinsed off the cells by washing 3× with cold PBS/0.2% Tween-20 solution. The cells were fixed with 4% PFA, as mentioned above, washed 1× with PBS, and resuspended in 1 mL of PBS. Cells were transferred to a 5 mL tube and subjected to flow-cytometric analysis. The median fluorescence intensity from each concentration of peptides was used to calculate the affinity constant. The equilibrium dissociation constants ($K_d=1/K_a$) of the peptide-cell interaction were obtained by fitting the data to the non-linear equation $I[X]=(I_0+I_{max}K_a[X])/(I_0+K_a[X])$. $I_0$ and $I_{max}$ are the initial and maximum fluorescence intensities, corresponding to no peptide and at saturation, respectively, and [X] represents the concentration of the bound peptide. Origin 6.1 data analysis software (Origin Lab Corp, Northampton, Mass.) was used to perform a non-linear least square fit of the data.

The relative fluorescence intensity as a function of the concentration of the fluorescent-labeled AKP-monomer and AKP-multimer peptides that bound to the HT29 cells was determined. A non-linear increase in fluorescence intensity with peptide concentration was observed until saturation was reached. A fit of the data with the model yields a $K_d=6.4$ nM/L, $R^2=0.973$ for the AKP-multimer and $K_d=310$ nM/L, $R^2=0.876$ for the AKP-monomer. Similar experiments performed with SW480 cell line also exhibited an improved binding affinity for the AKP-multimer, $K_d=101$ nM/L, $R^2=0.953$, in comparison to the AKP-monomer $K_d=1210$ nM/L, $R^2=0.933$. These results further support a multivalent approach to enhance the binding affinity of phage derived peptides through reconstruction of the phage architecture using trilysine core as a synthetic scaffold.

Kinetic Measurements

The binding kinetics for AKP-monomer and AKP-multimer peptide was further evaluated on the target cells in the presence of 10 µM peptide concentration. The target cells ($5\times10^5$) were detached and blocked as mentioned earlier and incubated with both monomer and multimer peptides at 4° C. over time from 0-60 min. After completing the incubation for each time course, the samples were prepared for flow cytometry, as mentioned above. The kinetics of peptide binding with the cell surface was determined by measuring the shift in the intensity of FITC-channel as a function of time. The resulting data were converted to median values as a function of time, and the rate constant was calculated using first order rate kinetics $Y=a-b^*\exp^{(-kx)}$; where a=maximum value, b=difference in intensity ($I-I_0$), and K=rate constant. Curve fits were performed using Origin 6.1 data analysis software.

The binding kinetics of AKP-multimer and AKP-monomer with HT29 cells on flow cytometry were measured. Binding of AKP-multimer with HT29 cells was ~2 fold faster (K=0.11364 min$^{-1}$; $R^2=0.972$), with kinetics comparable to that of the AKP-monomer (K=0.0663 min$^{-1}$; $R^2=0.984$). About 50% binding was observed at 5 min that seemed to become constant around 30 min and not changed even after incubating until 60 min. Even though the molecular weight of the AKP-multimer is about 2.3 fold greater than AKP-monomer, there was no slow down in reaction kinetics.

Statistical Analysis

Statistical analyses were calculated using Minitab software (Minitab Inc. State College, Pa.). First, the nonparametric Kruskal-Wallis test was used for each peptide to determine if observed differences were statistically significant among all peptides. The non-parametric Mann-Whitney test was used for comparisons between two independent samples. $p<0.05$ was considered to indicate a statistically significant difference.

Summary of Results

The multimer demonstrated increased fluorescence intensity from binding to colonic adenomas in vivo with a target/background ratio (TBR) of 3.84±0.26 compared to 2.21±0.13 for the monomer and 1.56±0.12 for the trilysine core, $p<0.001$. The FITC-labeled multimer showed greater fluorescence intensity on the surface of HT29 and SW480 cells on microscopy and higher counts on flow cytometry. Binding affinity to HT29 cells yielded a $K_d=6.4$ nM/L for multimer compared to $K_d=310$ nM/L for monomer. Measurements of binding kinetics with HT29 cells revealed K=0.1136 min$^{-1}$ to multimer compared to K=0.0663 min$^{-1}$ for monomer. Thus the use of multimer peptides can significantly improve binding affinity and kinetics for targeted detection of dysplastic colonic mucosa on fluorescence endoscopy.

The near-infrared (NIR) labeled multimer peptide can be used longitudinally to evaluate molecular expression in small animal models, and can also be directly translated into the clinic for early cancer detection.

While the present invention has been described in terms of specific embodiments, it is understood that variations and modifications will occur to those skilled in the art. Accordingly, only such limitations as appear in the claims should be placed on the invention.

All documents cited in this application are hereby incorporated by reference in their entirety.

We claim:

1. A peptide consisting of the amino acid sequence QPIHPNNM of SEQ ID NO: 1, KCCFPAQ of SEQ ID NO: 2, or a multimer form thereof.

2. A detectably labeled peptide consisting of the amino acid sequence QPIHPNNM of SEQ ID NO: 1, KCCFPAQ of SEQ ID NO: 2, or a multimer form thereof, wherein the detectable label attached to the peptide is a fluorophore or chemical tag.

3. The peptide of claim 2 wherein the fluorophore is fluorescein isothiocyanate (FITC).

4. The peptide of claim 2 wherein the fluorophore is Cy5 or Cy5.5.

5. The peptide of claim 2 wherein the flourophore is 7-Diethylaminocourmarin-3-carboxylic acid (DEAC).

6. The peptide of claim 2 wherein the fluorophore is 5-Carboxytetramethylrhodamine (TAMRA).

7. The peptide of claim 2 wherein the fluorophore is CF633.

8. A detectably labeled peptide consisting of the amino acid sequence QPIHPNNM of SEQ ID NO: 1, KCCFPAQ of SEQ ID NO: 2, or a multimer form thereof,
wherein the detectable label is attached to the peptide by a peptide linker and
wherein the detectable label is a fluorophore or chemical tag.

9. The peptide of claim 8 wherein a terminal amino acid of the linker is lysine.

10. The peptide of claim 9 wherein the linker comprises the sequence GGGSK of SEQ ID NO: 14.

11. A peptide consisting of the amino acid sequence QPIHPNNM of SEQ ID NO: 1, KCCFPAQ of SEQ ID NO: 2, or a multimer form thereof, wherein a detectable label is optionally attached to the peptide, and wherein a therapeutic moiety is attached to the peptide or the detectably labeled peptide.

12. The peptide of claim 11 wherein the therapeutic moiety is chemotherapeutic agent.

13. A composition comprising the peptide of any of the preceding claims and a pharmaceutically acceptable excipient.

14. A method for detecting colon dysplasia in a patient comprising the steps of administering the detectably labeled peptide of any of claims 2 through 11 or 12 to the colon of the patient and detecting binding of the detectably labeled peptide to dysplastic cells.

15. The method of claim 14 wherein the colon dysplasia is detected by the detectably labeled peptide consisting of the amino acid sequence QPIHPNNM of SEQ ID NO: 1.

16. The method of claim 14 wherein the colon dysplasia is detected by the detectably labeled peptide consisting of the amino acid sequence KCCFPAQ of SEQ ID NO: 2.

17. The method of claim 14 wherein cells of flat and depressed lesions are detected by the detectably labeled peptide KCCFPAQ of SEQ ID NO: 2.

18. A method of determining the effectiveness of a treatment for colon cancer and/or cancer metastasis, or recurrence of cancer in a patient comprising the step of administering the detectably labeled peptide of any of claims 2 through 11 or 12 to the colon of the patient, visualizing a first amount of cells labeled with the detectably labeled peptide, and comparing the first amount to a previously-visualized second amount of cells labeled with the detectably labeled peptide, wherein a decrease in the first amount cells labeled relative to the previously-visualized second amount of cells labeled is indicative of effective treatment.

19. The method of claim 12 further comprising obtaining a biopsy of the cells labeled by the detectably labeled peptide.

20. A method for delivering a therapeutic agent to dysplastic colon cells of a patient comprising the step of administering the peptide or detectably labeled peptide of any one of claims 11 or 12 to the patient.

21. A method for delivering a therapeutic agent to colon cancer cells of a patient comprising the step of administering the peptide or detectably labeled peptide of any one of claims 11 or 12 to the patient.

22. A kit for administering the composition of claim 13 to a patient in need thereof, said kit comprising the composition of claim 13, instructions for use of the composition and a device for administering the composition to the patient.

23. A peptide consisting of the amino acid sequence QPIHPNNM of SEQ ID NO: 1.

24. A detectably labeled peptide consisting of the amino acid sequence QPIHPNNM of SEQ ID NO: 1, KCCFPAQ of SEQ ID NO: 2, or a multimer form thereof, wherein the detectable label is attached to the peptide by a peptide linker and wherein the detectable label is Alexa Fluor 430 antibody conjugate pH 7.2, Alexa Fluor 488 antibody conjugate pH 8.0, Alexa Fluor 532 antibody conjugate pH 7.2, Alexa Fluor 555 antibody conjugate pH 7.2, Alexa Fluor 568 antibody conjugate pH 7.2, Alexa Fluor 610 R-phycoerythrin streptavidin pH 7.2, Alexa Fluor 647 antibody conjugate pH 7.2, Alexa Fluor 647 R-phycoerythrin streptavidin pH 7.2, Alexa Fluor 660 antibody conjugate pH 7.2, Alexa Fluor 680 antibody conjugate pH 7.2, Alexa Fluor 700 antibody conjugate pH 7.2, Allophycocyanin pH 7.5, AMCA conjugate, APC (allophycocyanin), BFP (Blue Fluorescent Protein), eCFP (Enhanced Cyan Fluorescent Protein), eGFP (Enhanced Green Fluorescent Protein), Eosin antibody conjugate pH 8.0, eYFP (Enhanced Yellow Fluorescent Protein), FITC antibody conjugate pH 8.0, FlAsH, Fluorescein antibody conjugate pH 8.0, Oregon Green 514 antibody conjugate pH 8.0, Pacific Blue antibody conjugate pH 8.0, Rhodamine Red-X antibody conjugate pH 8.0, Rhodol Green antibody conjugate pH 8.0, Tetramethylrhodamine antibody conjugate pH or Texas Red-X antibody conjugate pH 7.2.

\* \* \* \* \*

UNITED STATES PATENT AND TRADEMARK OFFICE
CERTIFICATE OF CORRECTION

| | | |
|---|---|---|
| PATENT NO. | : 8,901,276 B2 | Page 1 of 1 |
| APPLICATION NO. | : 13/329741 | |
| DATED | : December 2, 2014 | |
| INVENTOR(S) | : Thomas D. Wang et al. | |

It is certified that error appears in the above-identified patent and that said Letters Patent is hereby corrected as shown below:

In the claims,

At Column 57, line 52, "flourophore" should be -- fluorophore --.

At Column 57, line 63, "linker and" should be -- linker, and --.

At Column 60, line 2, "linker and" should be -- linker, and --.

Signed and Sealed this
First Day of March, 2016

Michelle K. Lee
*Director of the United States Patent and Trademark Office*

SEQUENCE LISTING

```
<160> NUMBER OF SEQ ID NOS: 34

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1

Gln Pro Ile His Pro Asn Asn Met
1               5
```

-continued

```
<210> SEQ ID NO 2
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2

Lys Cys Cys Phe Pro Ala Gln
1               5

<210> SEQ ID NO 3
<211> LENGTH: 18
<212> TYPE: PRT
<213> ORGANISM: Artificial Sequence
<220> FEATURE:
<223> OTHER INFORMATION: Synthetic peptide

<400> SEQUENCE: 3

Asn Gly Thr Thr Ser Ser Asn Asn Gln Leu Ile Asn Glu Asn Asn Ile
1               5                   10                  15

Gln Asn

<210> SEQ ID NO 4
<211> LENGTH: 18
<212> TYPE: PRT
<213> ORGANISM: Artificial Sequence
<220> FEATURE:
<223> OTHER INFORMATION: Synthetic peptide

<400> SEQUENCE: 4

Glu His Met Tyr Asn Thr Pro His Thr Tyr His Thr Thr Met Lys Asn
1               5                   10                  15

Asn Lys

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide

<400> SEQUENCE: 5

Asn Lys Leu Ala Ala Ala Leu Glu
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide

<400> SEQUENCE: 6

Lys Asn Tyr Lys Asn
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide
```

```
<400> SEQUENCE: 7

Thr Asn Thr His Asn
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide

<400> SEQUENCE: 8

Lys His Thr Asn Asn
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Ser Ile Leu Pro Tyr Pro Tyr
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide

<400> SEQUENCE: 10

Tyr Arg Ala Pro Trp Pro Pro
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide

<400> SEQUENCE: 11

Gln Pro Trp Pro Thr Ser Ile
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12

Trp Pro Thr Pro Pro Tyr Ala
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide
```

```
<400> SEQUENCE: 13

Met His Ala Pro Pro Phe Tyr
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic peptide

<400> SEQUENCE: 14

Gly Gly Gly Ser Lys
1               5

<210> SEQ ID NO 15
<211> LENGTH: 99
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
```

```
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t

<400> SEQUENCE: 15
aactgcaagc ttttamnnmn nmnnmnnmn mnnmnnmnnm nnmnnmnnmn nmnnmnnmnn    60
mnnmnnmnna ccaccaccag aattcggatc cccgagcat                         99

<210> SEQ ID NO 16
<211> LENGTH: 28
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (11)..(28)
<223> OTHER INFORMATION: Xaa can be any naturally occurring amino acid

<400> SEQUENCE: 16

Met Leu Gly Asp Pro Asn Ser Gly Gly Gly Xaa Xaa Xaa Xaa Xaa Xaa
1               5                   10                  15

Xaa Xaa Xaa Xaa Xaa Xaa Xaa Xaa Xaa Xaa Xaa Xaa
            20                  25

<210> SEQ ID NO 17
<211> LENGTH: 24
<212> TYPE: DNA
<213> ORGANISM: Artificial Sequence
<220> FEATURE:
<223> OTHER INFORMATION: Synthetic primer

<400> SEQUENCE: 17
atgctcgggg atccgaattc tggt                                        24

<210> SEQ ID NO 18
<211> LENGTH: 8
<212> TYPE: DNA
<213> ORGANISM: Artificial Sequence
<220> FEATURE:
<223> OTHER INFORMATION: Synthetic primer

<400> SEQUENCE: 18 gggaggga                                                           8

<210> SEQ ID NO 19
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 19
ccctcatagt tagcgtaacg                                               20

<210> SEQ ID NO 20
<211> LENGTH: 5
<212> TYPE: PRT
<213> ORGANISM: Artificial Sequence
<220> FEATURE:
<223> OTHER INFORMATION: Synthetic peptide

<400> SEQUENCE: 20

Lys Cys Cys Phe Pro
1               5

<210> SEQ ID NO 21
<211> LENGTH: 12
<212> TYPE: PRT
<213> ORGANISM: Artificial Sequence
<220> FEATURE:
<223> OTHER INFORMATION: Synthetic peptide

<400> SEQUENCE: 21

Gly Gly Gly Ala Gly Gly Gly Ala Gly Gly Gly Lys
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Synthetic peptide

<400> SEQUENCE: 22

Val Arg Pro Thr Leu Pro Met
1               5

<210> SEQ ID NO 23
<211> LENGTH: 12
<212> TYPE: PRT
<213> ORGANISM: Artificial Sequence
<220> FEATURE:
<223> OTHER INFORMATION: Synthetic peptide

<400> SEQUENCE: 23

Asn Phe Met Glu Ser Leu Pro Arg Leu Gly Met His
1               5                   10

<210> SEQ ID NO 24
<211> LENGTH: 4
<212> TYPE: PRT
<213> ORGANISM: Artificial Sequence
<220> FEATURE:
<223> OTHER INFORMATION: Synthetic peptide

<400> SEQUENCE: 24

His Tyr Lys Leu
1

<210> SEQ ID NO 25
<211> LENGTH: 7
<212> TYPE: PRT
<213> ORGANISM: Artificial Sequence
<220> FEATURE:
<223> OTHER INFORMATION: Synthetic peptide
```

```
<400> SEQUENCE: 25

Ala Lys Pro Gly Tyr Leu Ser
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic peptide

<400> SEQUENCE: 26

Leu Thr Thr His Tyr Lys Leu
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic peptide

<400> SEQUENCE: 27

Tyr Thr Thr Asn Lys His
1               5

<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28
ccctcatagt tagcgtaacg                                                   20

<210> SEQ ID NO 29
<211> LENGTH: 7
<212> TYPE: PRT
<213> ORGANISM: Artificial Sequence
<220> FEATURE:
<223> OTHER INFORMATION: Synthetic peptide

<400> SEQUENCE: 29

His Ala Ile Tyr Pro Arg His
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic peptide

<400> SEQUENCE: 30

Ala Leu Thr Pro Thr Pro Pro
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic peptide
```

```
<400> SEQUENCE: 31

Asn Leu Val Asn Leu Leu Pro
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide

<400> SEQUENCE: 32

Ala Asn Tyr Pro Arg Glu Pro
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic peptide

<400> SEQUENCE: 33

Ala Thr Thr Val Pro Ala Ser
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic peptide

<400> SEQUENCE: 34

Gly Gly Gly Ala Gly Gly Gly
1               5
```